(12) United States Patent
Noe et al.

(10) Patent No.: US 6,841,671 B2
(45) Date of Patent: Jan. 11, 2005

(54) SPIRO-PYRIMIDINE-2,4,6-TRIONE METALLOPROTEINASE INHIBITORS

(75) Inventors: Mark C. Noe, Mystic, CT (US); Martin J. Wythes, New London, CT (US); Brian S. Bronk, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/047,592

(22) Filed: Oct. 23, 2001

(65) Prior Publication Data

US 2003/0096803 A1 May 22, 2003

Related U.S. Application Data

(60) Provisional application No. 60/243,389, filed on Oct. 26, 2000.

(51) Int. Cl.[7] ............................................. C07D 487/10
(52) U.S. Cl. ...................... 544/231; 544/300; 544/301
(58) Field of Search ................................ 544/300, 301, 544/231

(56) References Cited

U.S. PATENT DOCUMENTS 3,714,093 A   1/1973   Wolf et al. ........... 260/251 QA

FOREIGN PATENT DOCUMENTS

| WO | WO 98/58925 | 12/1998 |
|----|-------------|---------|
| WO | WO 00/47565 | 8/2000  |
| WO | WO 01/12611 | 2/2001  |

OTHER PUBLICATIONS

USPTO Classification Definitions Re Heterocyclic 1985 Streitwieser et al., Introduction of Organic Chemistry 2nd Ed (1981) p. 1061 MacMillan Pub. Acheson "An Introduction to the Chemistry of Heterocyclic Compounds" (1976) p. 1 John Wiley Pub.*
PCT International Search Report, PCT/IB01/01986, 2001.

* cited by examiner

*Primary Examiner*—Richard L. Raymond
(74) *Attorney, Agent, or Firm*—Paul H. Ginsburg; Pamela C. Ancona; Steven R. Eck

(57) ABSTRACT

The present invention relates to 5-spiro-pyrimidine-2,4,6-trione metalloproteinase inhibitors of the formula

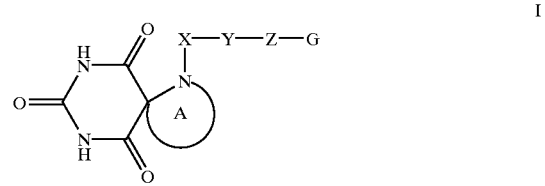

wherein said "A" is a 5–7 membered heterocyclic ring as defined in the specification and to pharmaceutical compositions and methods of treating inflammation, cancer and other disorders.

34 Claims, No Drawings

SPIRO-PYRIMIDINE-2,4,6-TRIONE METALLOPROTEINASE INHIBITORS

This application claims priority under 35 U.S.C. §119(e) of U.S. Provisional Application Ser. No. 60/243,389, filed Oct. 26, 2000.

BACKGROUND OF THE INVENTION

The present invention relates to 5-spiro-pyrimidine-2,4,6-trione metalloproteinase inhibitors and to pharmaceutical compositions and methods of treatment of inflammation, cancer and other disorders.

The compounds of the present invention are inhibitors of zinc metalloendopeptidases, especially those belonging to the class of matrix metalloproteinases (also called MMP or matrixin).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis rheumatoid arthritis.

It is recognized that different combinations of MMP's are expressed in different pathological situations. As such, inhibitors with specific selectivities for individual MMP's may be preferred for individual diseases.

Matrix metalloproteinase inhibitors are well known in the literature. Hydroxamic acid MMP inhibitors are exemplified in European Patent Publication 606,046, published Jul. 13, 1994. Several pyrimidine-2,4,6-trione MMP inhibitors are referred to in PCT publication WO 98/58925, published Dec. 30, 1998. PCT publication WO 00/47565, published Aug. 17, 2000 refers to certain aryl substituted pyrimidine-2,4,6-trione MMP inhibitors. U.S. Non-provisional application Ser. No. 09/635156, filed Aug. 9, 2000 (which claims priority to U.S. Provisional application 60/148547 filed Aug. 12, 1999) refers to heteroaryl substituted pyrimidine-2,4,6-trione MMP inhibitors. United States Provisional Application entitled "Pyrimidine-2,4,6-trione Metalloproteinase Inhibitors", filed Oct. 26, 2000, refers to certain pyrimidine-2,4,6-triones. Barbituric acids and methods for their preparation are well known in the art, see for example Goodman and Gilman's, *"The Pharmacological Basis of Therapeutics,"* 345–382 (Eighth Edition, McGraw Hill, 1990). Each of the above referenced publications and applications is hereby incorporated by reference in its entirety.

SUMMARY OF THE INVENTION

The present invention relates to compounds of the formula:

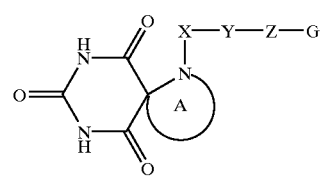

wherein said "A" is a 5–7 membered heterocyclic ring selected from the group consisting of:

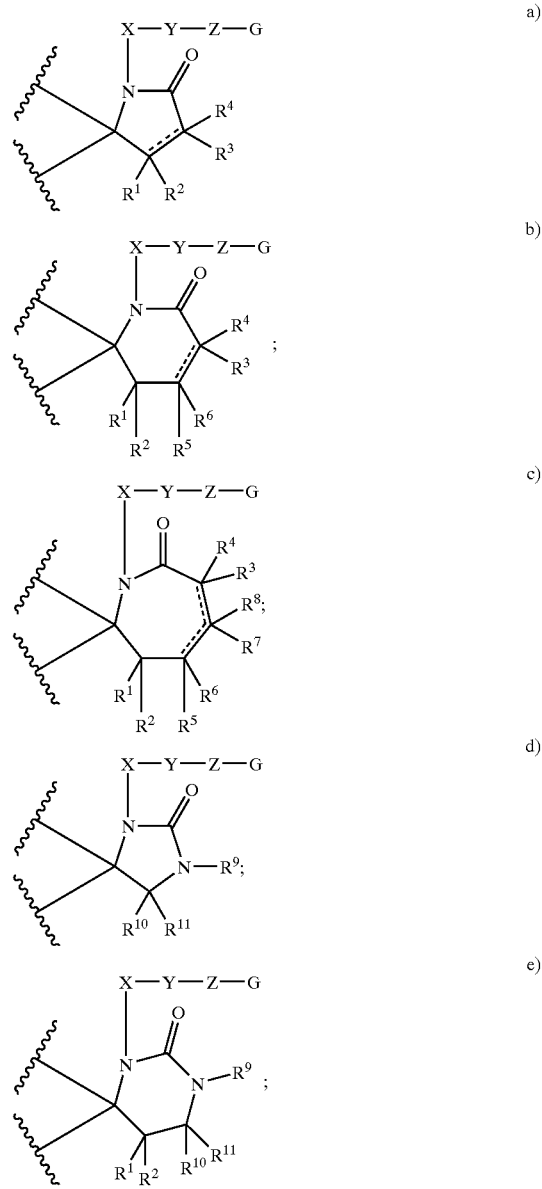

-continued

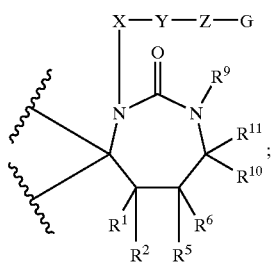

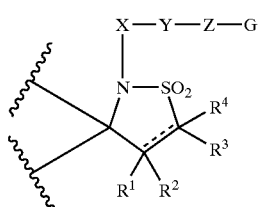

f) 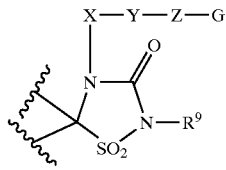

g) 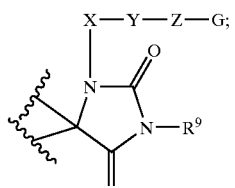

h)

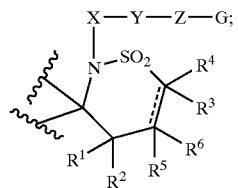

i)

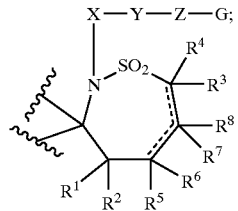

j)

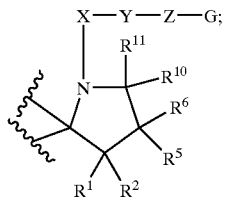

k)

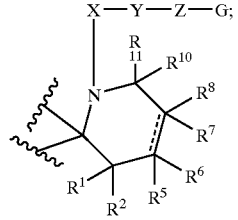

l)

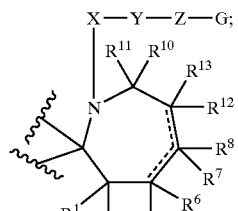

m)

n)

and o) 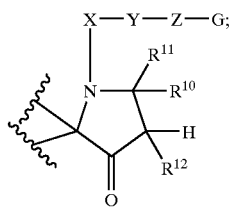

wherein
each of $R^1, R^2, R^3, R^4, R^5, R^6, R^7, R^8, R^9, R^{10}, R^{11}, R^{12}$ and $R^{13}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_8)$cycloalkyl and $(C_1-C_{10})$heterocyclyl; wherein each of said $(C_1-C_4)$alkyl, $(C_6-C_{10})$aryl, $(C_1-C_{10})$heteroaryl, $(C_3-C_8)$cycloalkyl and $(C_1-C_{10})$heterocyclyl may be optionally substituted on any of the ring carbon atoms capable of forming an additional bond with 1–3 substituents per ring independently selected from halo, $(C_1-C_4)$alkyl, $(C_1-C_4)$alkoxy, —CN, —OH and —NH$_2$;

X is $(C_6-C_{10})$aryl or $(C_1-C_{10})$heteroaryl;

Y is selected from the group consisting of a bond, oxygen, sulfur, >C=O, >SO$_2$, >S=O, —CH$_2$—, —CH$_2$O—, —O(CH$_2$)$_n$—, —CH$_2$S—, —S(CH$_2$)$_n$—, —CH$_2$SO—, —CH$_2$SO$_2$—, —SO(CH$_2$)$_n$—, —SO$_2$(CH$_2$)$_n$—, —NR$^{14}$, —NR$^{14}$(CH$_2$)$_n$—, —CH$_2$[N(R$^{14}$)]—, —CH$_2$(CH$_2$)$_n$—, —CH=CH—, —C≡C—, —[N(R$^{14}$)]—SO$_2$— and —SO$_2$[N(R$^{14}$)]—;

n is an integer from one to four;

$R^{14}$ is hydrogen or $(C_1-C_4)$alkyl;

Z is selected from the group consisting of $(C_6-C_{10})$aryl, $(C_3-C_8)$cycloalkyl, $(C_1-C_{10})$heterocyclyl and $(C_1-C_{10})$heteroaryl; wherein one or two carbon-carbon single bonds of said $(C_3-C_8)$cycloalkyl or $(C_1-C_{10})$heterocyclyl may optionally be replaced by carbon-carbon double bonds;

wherein each of said X or Z may be independently optionally substituted on any of the ring carbon atoms capable of forming an additional bond by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy;

G is $R^{15}$—(CR$^{16}$R$^{17}$)$_p$—; wherein G is a substituent on any ring carbon atom of Z capable of forming an additional bond and is oriented at a position other than alpha to the point of attachment of the Z ring to Y;

p is an integer from 0 to 4;

$R^{15}$ is independently selected from the group consisting of halo, —CN, —NO$_2$, OH, $(C_1-C_4)$alkenyl, $(C_1-C_4)$alkynyl, $(C_1-C_4)$perfluoroalkyl, perfluoro$(C_1-C_4)$alkoxy, $R^{18}$—, $R^{18}$—O—, $R^{18}$—$(C_1-C_4)$alkyl-O—, $R^{18}$—(C=O)—, $R^{18}$—(C=O)—O—, $R^{18}$—O—(C=O)—$R^{18}$—S—, $R^{22}$—(S=O)—, $R^{18}$—($SO_2$)—, $R^{22}$—($SO_2$)—($NR^{21}$)—, $R^{19}$—(C=O)—($NR^{21}$)—, $R^{22}$—O—(C=O)—($NR^{21}$)—, $(R^{19}R^{20})$N—, $(R^{19}R^{20})$N—($SO_2$)—, $(R^{19}R^{20})$N—(C=O)—; $(R^{19}R^{20})$N—(C=O)—($NR^{21}$)— and $(R^{19}R^{20})$N—(C=O)—O—;

each of $R^{16}$ and $R^{17}$ is independently selected from hydrogen and $(C_1-C_4)$alkyl;

or $R^{16}$ and $R^{17}$ may optionally be taken together with the carbon to which they are attached to form a 5 to 10-membered carbocyclic ring;

$R^{18}$, $R^{19}$, $R^{20}$ and $R^{21}$ are independently selected from the group consisting of hydrogen, $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—;

or $R^{19}$ and $R^{20}$ may optionally be taken together with the nitrogen to which they are attached to form a 3 to 8-membered heterocyclic ring;

or $R^{19}$ and $R^{21}$ may optionally be taken together with the nitrogen, the carbon or the oxygen to which they are attached to form a 3 to 8-membered heterocyclic ring;

$R^{22}$ is selected from the group consisting of $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—;

or $R^{21}$ and $R^{22}$ may optionally be taken together with the nitrogen, the oxygen or the sulfur to which they are attached to form a 3 to 8-membered heterocyclic ring;

or the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine) and the lower alkanolammonium and other base salts of pharmaceutically acceptable organic amines.

The term "a bond", as used herein in the group Y, means that the groups X and Z are directly connected through a carbon-carbon bond so as to form pendent aryl rings such as diphenyl.

The dashed lines as used in each of the heterocyclic ring "A" of formulae a), b), c), g), h), i), k) and l) refer to optional double bonds. The exact positions of the optional double bonds for each of the heterocyclic ring "A" of formulae a), b), c), g), h), i), k) and l) are as defined in the specification. Whenever the dashed line extends over two carbon atoms, one skilled in the art will understand that two carbons are tetravalent and that the extra substituent(s) (i.e., any of $R^1$, $R^2$, $R^3$, $R^4$, $R^5$, $R^6$, $R^7$, $R^8$, $R^{10}$, $R^{11}$, $R^{12}$, or $R^{13}$) may be absent.

The term "alkyl", as used herein, unless otherwise indicated, includes saturated monovalent hydrocarbon radicals having straight, branched moieties, or combinations thereof. Alkyl groups, wherever they occur, may be optionally substituted by a suitable substituent.

The term "alkenyl", as used herein, unless otherwise indicated, includes hydrocarbon radicals containing at least one olefin linkage and having straight, branched moieties, or combinations thereof.

The term "alkynyl", as used herein, unless otherwise indicated, includes hydrocarbon radicals containing at least one carbon-carbon triple bond linkage and having straight, branched moieties or combinations thereof.

The term "cycloalkyl", as used herein, unless otherwise indicated, includes a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds and optionally substituted by 1 to 3 suitable substituents as defined below such as fluoro, chloro, trifluoromethyl, $(C_1-C_4)$alkoxy, $(C_6-C_{10})$aryloxy, trifluoromethoxy, difluoromethoxy or $(C_1-C_4)$alkyl, more preferably fluoro, chloro, methyl, ethyl and methoxy.

The term "alkoxy", as used herein, includes O-alkyl groups wherein "alkyl" is as defined above.

The term "halo", as used herein, unless otherwise indicated, includes fluorine, chlorine, bromine or iodine, preferably fluorine or chlorine.

The term "aryl", as used herein, unless otherwise indicated, includes an organic radical derived from an aromatic hydrocarbon by removal of one or more hydrogens, such as phenyl or naphthyl, optionally substituted by 1 to 3 suitable substituents such as fluoro, chloro, cyano, nitro, trifluoromethyl, $(C_1-C_6)$alkoxy, $(C_6-C_{10})$aryloxy, $(C_3-C_8)$cycloalkyloxy, trifluoromethoxy, difluoromethoxy, or $(C_1-C_6)$alkyl.

The term "heteroaryl", as used herein, unless otherwise indicated, includes an organic radical derived from an aromatic heterocyclic compound by removal of one or more hydrogens, such as benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy. The foregoing groups, can be C-attached or N-attached where such is possible. For instance, pyrrolyl can be pyrrol-1-yl (N-attached) or pyrrol-3-yl (C-attached).

The term "heterocyclyl", as used herein, unless otherwise indicated, includes an organic radical derived from a non-aromatic heterocyclic compound by removal of one or more hydrogens, such as 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl and trithianyl. The foregoing groups, can be C-attached or N-attached where such is possible. For example, piperidinyl can be piperidin-1-yl (N-attached) or piperidin-4-yl (C-attached). The foregoing groups, as derived from the compounds listed above, can be optionally substituted where such is possible by a suitable substituent, such as oxo, F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, or $(C_3-C_8)$cycloalkyloxy.

The phrase "a suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, an arylsulfonyl groups and the like.

The phrase "at a position other than alpha to the point of attachment of the Z ring to Y", as used herein, unless otherwise indicated, is intended to mean a chemically and pharmaceutically acceptable orientation of the bond connecting group Z to G (Z-G bond) relative to the bond connecting group Y to Z (Y-Z bond). Such relative orientation may be meta, wherein the Z-G bond is in the 1,3 position relative to the Y-Z bond. Another relative orientation may be para, wherein the Z-G bond is in the 1,4 position relative to the Y-Z bond.

Some compounds of formula I contain chiral centers and therefore exist in different enantiomeric forms. This invention relates to all optical isomers, enantiomers, diastereomers and stereoisomers of the compounds of formula I and mixtures thereof. The compounds of the invention also exist in different tautomeric forms. This invention relates to all tautomers of formula I. Those skilled in the art are well aware that the pyrimidine-2,4,6-trione nucleus exists as a mixture of tautomers in solution. The various ratios of the tautomers in solid and liquid form is dependent on the various substituents on the molecule as well as the particular crystallization technique used to isolate a compound.

In one embodiment of the invention, the heterocyclic ring "A" of the compounds of the formula I is selected from the formulae a) or b):

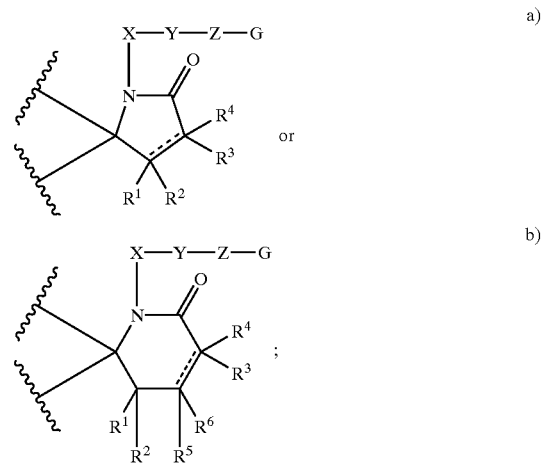

wherein X is $(C_6-C_{10})$aryl, preferably phenyl. Within this embodiment, Y is selected from the group consisting of a bond, oxygen, $>C=O$, $-CH_2-$, $-CH_2O-$, $-O(CH_2)_n-$, $-CH_2CH_2-$, $-CH=CH-$ and $-C\equiv C-$; wherein n is 1 or 2; preferably Y is selected from the group consisting of oxygen, $-OCH_2-$ and $-CH_2O-$; more preferably Y is oxygen.

In another embodiment of the invention, the heterocyclic ring "A" has the formulae a) or b), wherein X is $(C_6-C_{10})$ aryl, preferably phenyl. Within this embodiment, Y is selected from the group consisting of sulfur, $>SO_2$, $>S=O$, $-CH_2S-$, $-S(CH_2)_n-$, $-CH_2SO-$, $-CH_2SO_2-$, $-SOCH_2-$ and $-SO_2(CH_2)_n-$; wherein n is 1 or 2; preferably Y is sulfur or $>SO_2$.

In another embodiment of the invention, the heterocyclic ring "A" has the formulae a) or b), wherein X is $(C_6-C_{10})$ aryl, preferably phenyl. Within this embodiment, Y is selected from the group consisting of $CH_2[N(R^{14})]-$, $>NR^{14}$, $-NR^{14}(CH_2)_n-$, $-SO_2[N(R^{14})]-$ and $-[N(R^{14})]-SO_2-$, wherein $R^{14}$ is hydrogen or methyl; and n is 1 or 2.

In another embodiment of the invention, the heterocyclic ring "A" has the formulae a) or b), wherein X is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy; preferably X is selected from the group consisting of imidazolyl, isothiazolyl, isoxazolyl, oxadiazolyl, oxazolyl, pyrazinyl, pyridazinyl, pyridinyl, pyrimidinyl and pyrazolyl; more preferably X is pyrazinyl, pyridazinyl, pyridyl and pyrimidinyl; most preferably X is pyridinyl. Within this embodiment, Y is a bond, oxygen, sulfur, —CH$_2$—, >SO$_2$, —OCH$_2$— or —CH$_2$O—; preferably Y is oxygen, —OCH$_2$— or —CH$_2$O—; more preferably Y is oxygen.

In another embodiment of the invention, the heterocyclic ring "A" has the formulae a) or b), wherein X is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy; preferably X is selected from the group consisting of imidazolyl, isothiazolyl, isoxazolyl, oxadiazolyl, oxazolyl, pyrazinyl, pyridazinyl, pyridinyl, pyrimidinyl and pyrazolyl; more preferably X is pyrazinyl, pyridazinyl, pyridyl and pyrimidinyl; most preferably X is pyridinyl. Within this embodiment, Y is selected from the group consisting of sulfur, >SO$_2$, >S=O, —CH$_2$S—, —S(CH$_2$)$_n$—, —CH$_2$SO—, —CH$_2$SO$_2$—, —SOCH$_2$— and —SO$_2$(CH$_2$)$_n$—; wherein n is 1 or 2; preferably Y is sulfur or >SO$_2$.

In another embodiment of the invention, the heterocyclic ring "A" has the formulae a) or b), wherein X is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy; preferably X is selected from the group consisting of imidazolyl, isothiazolyl, isoxazolyl, oxadiazolyl, oxazolyl, pyrazinyl, pyridazinyl, pyridinyl, pyrimidinyl and pyrazolyl; more preferably X is pyrazinyl, pyridazinyl, pyridyl and pyrimidinyl; most preferably X is pyridinyl. Within this embodiment Y is selected from the group consisting of CH$_2$[N(R$^{14}$)]—, >NR$^{14}$, —NR$^{14}$(CH$_2$)$_n$—, —SO$_2$[N(R$^{14}$)]— and —[N(R$^{14}$)]—SO$_2$—, wherein R$^{14}$ is hydrogen or methyl; and n is 1 or 2.

In another embodiment of the invention, the heterocyclic ring "A" has the formula a), wherein X is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy; preferably X is selected from the group consisting of imidazolyl, isothiazolyl, isoxazolyl, oxadiazolyl, oxazolyl, pyrazinyl, pyridazinyl, pyridinyl, pyrimidinyl and pyrazolyl; more preferably X is pyrazinyl, pyridazinyl, pyridyl and pyrimidinyl; most preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula a), as defined in the aforesaid paragraph, wherein in the heterocyclic ring "A" the dashed line is a double bond.

In another embodiment of the invention, the heterocyclic ring "A" has the formula b), wherein X is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy; preferably X is selected from the group consisting of imidazolyl, isothiazolyl, isoxazolyl, oxadiazolyl, oxazolyl, pyrazinyl, pyridazinyl, pyridinyl, pyrimidinyl and pyrazolyl; more preferably X is pyrazinyl, pyridazinyl, pyridyl and pyrimidinyl; most preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula b), as defined in the aforesaid paragraph, wherein in the heterocyclic ring "A" the dashed line is a double bond.

In another embodiment of the invention, the heterocyclic ring "A" has the formula c):

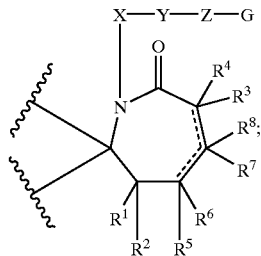

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is selected from the group consisting of pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula c), wherein in the heterocyclic ring "A" the dashed line is a double bond, such that the heterocyclic ring "A" of formula c is selected from the group consisting of:

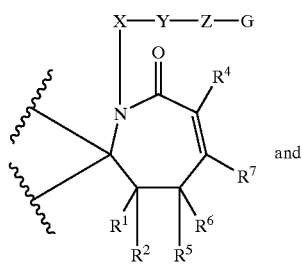

c$_1$)

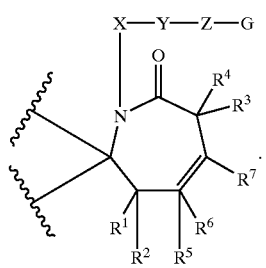

c$_2$)

In another embodiment of the invention, the heterocyclic ring "A" has the formula d):

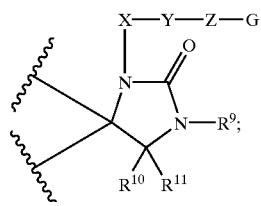

d)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula e):

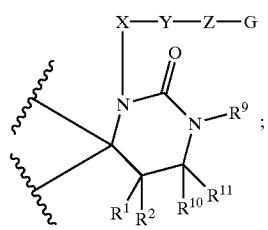

e)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula f):

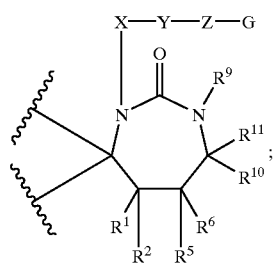

f)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula g):

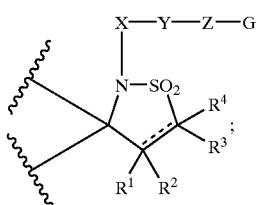

g)

wherein X is ($C_1$–$C_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —$CH_2$—, >$SO_2$, —$OCH_2$— and —$CH_2O$—; preferably Y is oxygen, —$OCH_2$— or —$CH_2O$—; more preferably Y is oxygen.

In another embodiment of the invention, the heterocyclic ring "A" has the formula g), as defined in the aforesaid paragraph, wherein in the heterocyclic ring "A" the dashed line is a double bond.

In another embodiment of the invention, the heterocyclic ring "A" has the formula h):

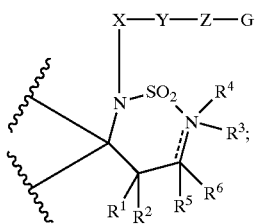

h)

wherein X is ($C_1$–$C_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —$CH_2$—, >$SO_2$, —$OCH_2$— and —$CH_2O$—; preferably Y is oxygen, —$OCH_2$— or —$CH_2O$—; more preferably Y is oxygen.

In another embodiment of the invention, the heterocyclic ring "A" has the formula h), as defined in the aforesaid paragraph, wherein in the heterocyclic ring "A" the dashed line is a double bond.

In another embodiment of the invention, the heterocyclic ring "A" has the formula i):

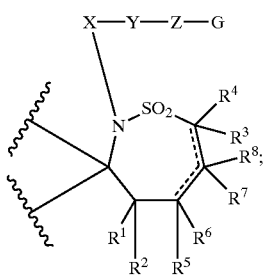

i)

wherein X is ($C_1$–$C_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —$CH_2$—, >$SO_2$, —$OCH_2$— and —$CH_2O$—; preferably Y is oxygen, —$OCH_2$— or —$CH_2O$—; more preferably Y is oxygen.

In another embodiment of the invention, the heterocyclic ring "A" has the formula i), wherein in the heterocyclic ring "A" the dashed line is a double bond, such that the heterocyclic ring "A" of formula i) is selected from the group consisting of:

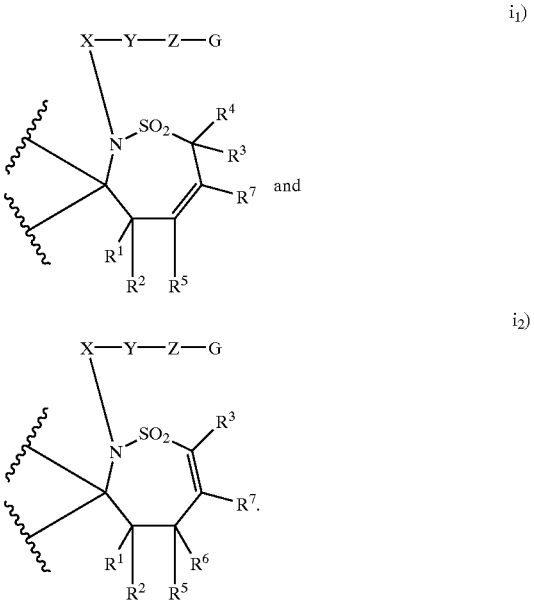

$i_1$)

and

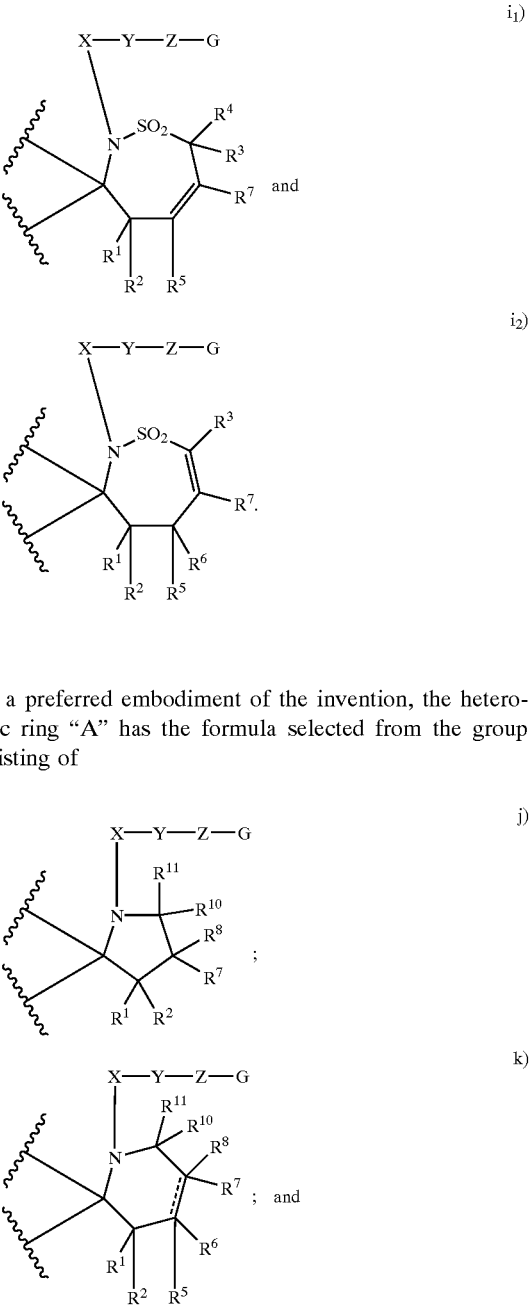

$i_2$)

In a preferred embodiment of the invention, the heterocyclic ring "A" has the formula selected from the group consisting of j)

k)

; and

-continued

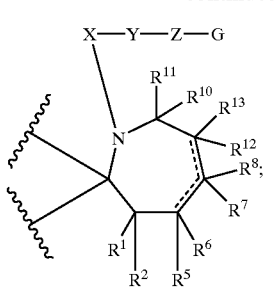

l)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another preferred embodiment of the invention, the heterocyclic ring "A" has the formula j):

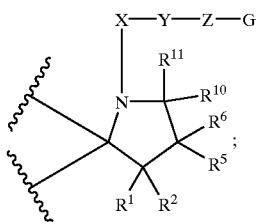

j)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another preferred embodiment of the invention, the heterocyclic ring "A" has the formula k):

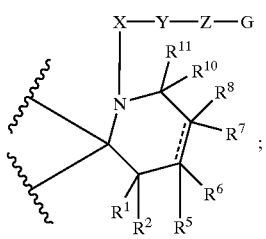

k)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula k), as defined in the aforesaid paragraph, wherein in the heterocyclic ring "A" the dashed line is a double bond.

In another preferred embodiment of the invention, the heterocyclic ring "A" has the formula l):

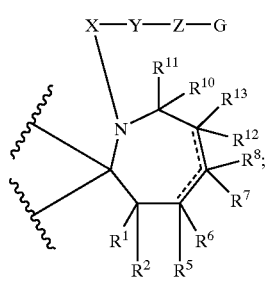

l)

wherein X is (C$_1$–C$_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —CH$_2$—, >SO$_2$, —OCH$_2$— and —CH$_2$O—; preferably Y is oxygen, —OCH$_2$— or —CH$_2$O—; more preferably Y is oxygen.

In another embodiment of the invention, the heterocyclic ring "A" has the formula l), wherein in the heterocyclic ring "A" the dashed line is a double bond, such that the heterocyclic ring "A" of formula l is selected from the group consisting of:

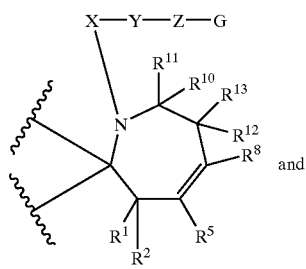

l$_1$)

and

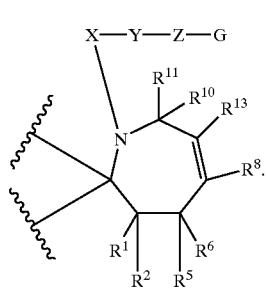

l$_2$)

In another embodiment of the invention, the heterocyclic ring "A" has the formula m):

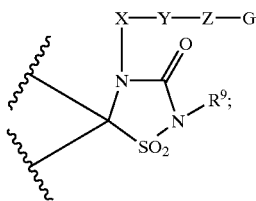

wherein X is ($C_1$–$C_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —$CH_2$—, >$SO_2$, —$OCH_2$— and —$CH_2O$—; preferably Y is oxygen, —$OCH_2$— or —$CH_2O$—; more preferably Y is oxygen.

In another embodiment of the invention, the heterocyclic ring "A" has the formula n):

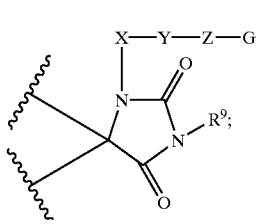

wherein X is ($C_1$–$C_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —$CH_2$—, >$SO_2$, —$OCH_2$— and —$CH_2O$—; preferably Y is oxygen, —$OCH_2$— or —$CH_2O$—; more preferably Y is oxygen.

In another embodiment of the invention, the heterocyclic ring "A" has the formula o):

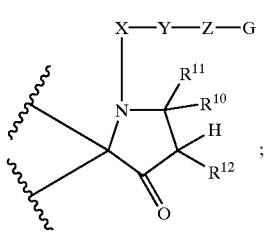

wherein X is ($C_1$–$C_{10}$)heteroaryl selected from the group consisting of imidazolyl, isothiazolyl, isoxazolyl, oxadiazolyl, oxazolyl, pyrazinyl, pyridazinyl, pyridinyl, pyrimidinyl and pyrazolyl; preferably X is pyrazinyl, pyridazinyl, pyridyl and pyrimidinyl; more preferably X is pyridinyl. Within this embodiment, Y is selected from the group consisting of a bond, oxygen, sulfur, —$CH_2$—, >$SO_2$, —$OCH_2$— and —$CH_2O$—; preferably Y is oxygen, —$OCH_2$— or —$CH_2O$—; more preferably Y is oxygen.

In another embodiment of the invention, each of $R^1$, $R^2$, $R^3$, $R^4$, $R^{10}$, $R^{11}$, $R^{12}$ and $R^{13}$ is selected from the group consisting of hydrogen, ($C_1$–$C_4$)alkyl, ($C_1$–$C_4$)alkenyl, ($C_1$–$C_4$)alkynyl, ($C_6$–$C_{10}$)aryl, ($C_1$–$C_{10}$)heteroaryl, ($C_3$–$C_8$)cycloalkyl and ($C_1$–$C_{10}$)heterocyclyl; and wherein each of said ($C_1$–$C_4$)alkyl, ($C_6$–$C_{10}$)aryl, ($C_1$–$C_{10}$)heteroaryl, ($C_3$–$C_8$)cycloalkyl and ($C_1$–$C_{10}$)heterocyclyl may be optionally substituted on any of the ring carbon atoms capable of forming an additional bond with 1–3 substituents independently selected from halo, ($C_1$–$C_4$)alkyl, ($C_1$–$C_4$)alkoxy, —CN, —OH and —$NH_2$.

A generic or sub-generic embodiment of each of the foregoing embodiments are those compounds wherein each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is selected from the group consisting of hydrogen, ($C_1$–$C_4$)alkyl, ($C_6$–$C_{10}$)aryl, ($C_1$–$C_{10}$)heteroaryl, and ($C_3$–$C_8$)cycloalkyl.

A preferred generic or sub-generic embodiment is directed to those foregoing embodiments wherein each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is selected from hydrogen and ($C_1$–$C_4$)alkyl, such as methyl.

In another embodiment of the invention, each of $R^5$, $R^6$, $R^7$ and $R^8$ is selected from the group consisting of hydrogen, ($C_1$–$C_4$)alkyl, ($C_1$–$C_4$)alkenyl, ($C_1$–$C_4$)alkynyl, ($C_6$–$C_{10}$)aryl, ($C_1$–$C_{10}$)heteroaryl, ($C_3$–$C_8$)cycloalkyl and ($C_1$–$C_{10}$)heterocyclyl; and wherein each of said ($C_1$–$C_4$)alkyl, ($C_6$–$C_{10}$)aryl, ($C_1$–$C_{10}$)heteroaryl, ($C_3$–$C_8$)cycloalkyl and ($C_1$–$C_{10}$)heterocyclyl may be optionally substituted on any of the ring carbon atoms capable of forming an additional bond with 1–3 substituents independently selected from halo, ($C_1$–$C_4$)alkyl, ($C_1$–$C_4$)alkoxy, —CN, —OH and —$NH_2$.

In another embodiment of the invention, one or two of $R^5$, $R^6$, $R^7$ and $R^8$ is/are a group other than hydrogen.

In another embodiment of the invention, $R^9$ is independently selected from hydrogen, ($C_1$–$C_4$)alkyl, ($C_6$–$C_{10}$)aryl, ($C_1$–$C_{10}$)heteroaryl, ($C_3$–$C_8$)cycloalkyl and ($C_1$–$C_{10}$)heterocyclyl.

In another embodiment of the invention, $R^9$ is independently selected from hydrogen and ($C_1$–$C_4$)alkyl, such as methyl.

In another embodiment of the invention, Z is a ($C_3$–$C_8$)cycloalkyl or a ($C_1$–$C_{10}$)heterocyclyl, selected from the group consisting of cyclopropyl, cyclobutyl, cyclopentyl, cyclohexyl, tetrahydrofuranyl, tetrahydropyranyl, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolidin-2,4-dion-5-yl, 1,2-pyrazolidin-3-on-4-yl, tetrahydro-1,3-oxazin-4-on-5-yl, tetrahydro-1,3-oxazi-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2,4-oxadiazin-5-on-6-yl, 5,6-dihydro-1-2,4-oxadiazin-5-on-6-yl, 1,2,4-oxadiazin-3,5-dion-6-yl and 1,2,4-triazin-6-on-5-yl. Within this embodiment, preferably Z is selected from the group consisting of cyclopropyl, cyclobutyl, cyclopentyl, cyclohexyl, tetrahydrofuranyl, tetrahydropyranyl, N-methyl-3-azetidinyl, piperazinyl, piperidinyl, N-methylpiperidinyl and morpholinyl. Within this embodiment, more preferably Z is selected from the group consisting of cyclopropyl, cyclobutyl, cyclopentyl, cyclohexyl, tetrahydrofuranyl and tetrahydropyranyl. Within this embodiment, most preferably Z is selected from the group consisting of cyclopentyl, cyclohexyl, tetrahydrofuranyl and tetrahydropyranyl.

In another embodiment of the invention, Z is a $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, more preferably pyridinyl, pyrazinyl, pyridazinyl and pyrazolyl, wherein said $(C_1-C_{10})$heteroaryl is optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy.

In another embodiment of the invention, either X or Z is substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy.

In another embodiment of the invention, both X and Z are substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy.

In another embodiment of the invention, G is $R^{15}$—$(CR^{16}R^{17})_p$—; wherein p is 0; $R^{15}$ is selected from the group consisting of halo, —CN, and $R^{18}$; wherein said $R^{18}$ is selected from the group consisting hydrogen, $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl(C=O)—.

In another embodiment of the invention, G is $R^{15}$—$(CR^{16}R^{17})_p$—; wherein p is 0 to 4, preferably 1 to 2; $R^{15}$ is selected from the group consisting of halo, —CN, —NO$_2$, OH, $(C_1-C_4)$alkenyl, $(C_1-C_4)$alkynyl, $(C_1-C_4)$perfluoroalkyl, perfluoro$(C_1-C_4)$alkoxy, $R^{18}$—, $R^{18}$—O—, $R^{18}$—$(C_1-C_4)$alkyl-O—, $R^{18}$—(C=O)—, $R^{18}$—(C=O)—O—, $R^{18}$—O—(C=O)—, $R^{18}$—S—, $R^{22}$—(S=O)—, $R^{18}$—(SO$_2$)—, $R^{22}$—(SO$_2$)—(NR$^{21}$)—, $R^{19}$—(C=O)—(NR$^{21}$)—, $R^{22}$—O—(C=O)—(NR$^{21}$)—, $(R^{19}R^{20})$N—, $(R^{19}R^{20})$N—(SO$_2$)—, $(R^{19}R^{20})$N—(C=O)—; $(R^{19}R^{20})$N—(C=O)—(NR$^{21}$)— and $(R^{19}R^{20})$N—(C=O)—O; each of $R^{16}$ and $R^{17}$ is independently hydrogen or $(C_1-C_4)$alkyl; $R^{18}$ is selected from the group consisting hydrogen, $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—.

In another embodiment of the invention, G is $R^{15}$—$(CR^{16}R^{17})_p$—; wherein p is 1; $R^{15}$ is $(R^{19}R^{20})$N—; each of $R^{16}$ or $R^{17}$ is independently hydrogen; and each of $R^{19}$ and $R^{20}$ is hydrogen or $(C_1-C_{10})$heteroaryl, such as 2-oxazolyl, 2-pyrazolyl, or 3-pyrazolyl.

In another embodiment of the invention, G is $R^{15}$—$(CR^{16}R^{17})_p$—; wherein p is 1; $R^{15}$ is $(R^{19}R^{20})$N—(C=O)—(NR$^{21}$)—; each of $R^{16}$ or $R^{17}$ is independently hydrogen; each of $R^{19}$ and $R^{20}$ is $(C_1-C_4)$alkyl and are taken together with the nitrogen to which they are attached to form a 3 to 8-membered ring; and wherein $R^{23}$ is selected from the group consisting of hydrogen and $(C_1-C_4)$alkyl.

In another embodiment of the invention, G is $R^{15}$—$(CR^{16}R^{17})_p$—; wherein p is 1; $R^{15}$ is $R^{22}$—O—(C=O)—(NR$^{21}$)—; each of $R^{16}$ or $R^{17}$ is independently hydrogen; $R^{21}$ is selected from the group consisting of hydrogen and $(C_1-C_4)$alkyl; and wherein $R^{22}$ is selected from the group consisting of $(C_1-C_4)$alkyl and $(C_3-C_8)$cycloalkyl, such as methyl, ethyl, propyl, butyl or cyclobutyl.

In another embodiment of the invention G is $R^{15}$—$(CR^{16}R^{17})_p$—; wherein p is 1; $R^{15}$ is $R^{19}$—(C=O)—(NR$^{21}$); each of $R^{16}$ and $R^{17}$ is independently hydrogen or $(C_1-C_4)$alkyl; $R^{19}$ and $R^{21}$ are taken together with the carbon or the nitrogen to which they are attached to form a 3 to 8 membered heterocyclic ring.

In another embodiment of the invention, G is $R^{15}$—$(CR^{16}R^{17})_p$—; wherein p is 1; $R^{15}$ is $(R^{19}R^{20})$N—(C=O)—(NR$^{21}$); each of $R^{16}$ and $R^{17}$ is independently hydrogen or $(C_1-C_4)$alkyl; $R^{19}$ and $R^{21}$ are taken together with the nitrogen to which they are attached to form a 3 to 8 membered heterocyclic ring.

In another embodiment of the invention, G is $R^{15}$—$(CR^{16}R^{17})_p$—; wherein p is 1; $R^{15}$ is $R^{22}$—O—(C=O)—(NR$^{21}$)—; each of $R^{16}$ and $R^{17}$ is independently hydrogen or $(C_1-C_4)$alkyl; $R^{21}$ and $R^{22}$ are taken together with the nitrogen or the oxygen to which they are attached to form a 3 to 8 membered heterocyclic ring.

In another embodiment of the invention, G is $R^{15}$—$(CR^{16}R^{17})_p$—; wherein p is 1 to 4, preferably 1; $R^{15}$ is selected from the group consisting of halo, —CN and $R^{18}$; each of $R^{16}$ and $R^{17}$ is independently hydrogen or $(C_1-C_4)$alkyl; said $R^{18}$ is selected from the group consisting of hydrogen, $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$ alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—.

In another embodiment of the invention, G is $R^{15}$—$(CR^{16}R^{17})_p$—; wherein p is 1 to 4, preferably 1; $R^{15}$ is selected from the group consisting of $R^{18}$; each of $R^{16}$ and $R^{17}$ is independently hydrogen or $(C_1-C_4)$alkyl; wherein said $R^{18}$ is selected from the group consisting of hydrogen and $(C_1-C_4)$alkyl.

In another embodiment of the invention, G is $R^{15}$—$(CR^{16}R^{17})_p$—; wherein p is 1 to 4, preferably 1; $R^{15}$ is selected from the group consisting of $(R^{19}R^{20})N$—, $(R^{19}R^{20})N$—(C=O), $(R^{19}R^{20})N$—(SO$_2$); $(R^{19}R^{20})N$—(C=O)—(NR$^{21}$)— and $(R^{19}R^{20})N$—(C=O)—O; each of $R^{16}$ and $R^{17}$ is independently hydrogen or $(C_1-C_4)$alkyl; and wherein $R^{19}$ and $R^{20}$ are taken together with the nitrogen to which they are attached to form a 3 to 8-membered heterocyclic ring.

In another embodiment of the invention, G is $R^{15}$—$(CR^{16}R^{17})_p$—; wherein p is 1 to 4, preferably 1; $R^{15}$ is selected from the group consisting of $R^{19}$—(C=O)—(NR$^{21}$)—, $(R^{19}R^{20})N$—(C=O)—(NR$^{21}$), —NR$^{19}R^{20}$, $(R^{19}R^{20})N$—(C=O)—(NR$^{21}$)—; $R^{22}$(S=O)—; $R^{22}$(SO$_2$)—(NR$^{21}$)—; $R^{22}$—O—(C=O)—(NR$^{21}$)— and $(R^{19}R^{20})N$—(C=O)—O—; each of $R^{16}$ and $R^{17}$ is independently hydrogen or $(C_1-C_4)$alkyl; wherein each of $R^{19}$, $R^{20}$ and $R^{21}$ is independently selected from the group consisting of hydrogen, $(C_1-C_4)$alkyl, $(C_6-C_{10})$aryl, $(C_3-C_8)$cycloalkyl, $(C_1-C_{10})$heteroaryl and $(C_1-C_{10})$ heterocyclyl; wherein the $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by 1–3 substituents independently selected from F, Cl, Br, CN, OH, $(C_1-C_4)$ alkyl, $(C_1-C_4)$perfluoroalkyl, $(C_1-C_4)$perfluoroalkoxy, $(C_1-C_4)$alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—; and wherein $R^{22}$ is selected from the group consisting of $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein the $(C_6-C_{10})$aryl, $(C_3-C_8)$ cycloalkyl, $(C_1-C_{10})$heteroaryl and $(C_1-C_{10})$heterocyclyl moieties may be optionally substituted on any of the ring carbon atoms capable of forming an additional bond by 1–3 substituents independently selected from F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy, amino, $(C_1-C_4)$alkyl-NH—, $[(C_1-C_4)$alkyl$]_2$-N— and $(_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—.

In another embodiment of the invention, G is $R^{15}$—$(CR^{16}R^{17})_p$—; wherein p is 1 to 4, preferably 1; $R^{15}$ is selected from the group consisting of $R^{19}$—(C=O)—(NR$^{21}$)—, $R^{19}$—O—(C=O)—(NR$^{21}$)— and $(R^{19}R^{20})N$—(C=O)—(NR$^{21}$); each of $R^{16}$ and $R^{17}$ is independently hydrogen or $(C_1-C_4)$alkyl; wherein $R^{19}$ and $R^{21}$ are taken together with the nitrogen, the carbon or the oxygen to which they are attached to form a 3 to 8 membered heterocyclic ring.

In another embodiment of the invention, G is $R^{15}$—$(CR^{16}R^{17})_p$—; wherein p is 0; and G is oriented at a position other than alpha to the point of attachment of the Z ring to Y.

In another embodiment of the invention, G is $R^{15}$—$(CR^{16}R^{17})_p$—; wherein p is 0; and G is oriented at a position meta to the point of attachment of the Z ring to Y.

In another embodiment of the invention, G is $R^{15}$—$(CR^{16}R^{17})_p$—; wherein p is 1 to 4, preferably 1; and G is oriented at a position other than alpha to the point of attachment of the Z ring to Y.

In another embodiment of the invention, G is $R^{15}$—$(CR^6R^{17})_p$—; wherein p is 1 to 4, preferably 1; and G is oriented at a position meta to the point of attachment of the Z ring to Y.

In another preferred embodiment of the invention, one or two of $R^1$, $R^2$, $R^3$, $R^4$, $R^{10}$, $R^{11}$, $R^{12}$ and $R^{13}$ is a group other than hydrogen.

In a more preferred embodiment of the invention, each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is hydrogen.

In another preferred embodiment of the invention, either X or Z is not substituted by any optional substituents.

In another preferred embodiment of the invention, both X and Z are not substituted by any optional substituents.

In another preferred embodiment of the invention, G is $R^{15}$—$(CR^{16}R^{17})_p$—; wherein p is 0; $R^{15}$ is selected from the group consisting of halo, —CN and $(C_1-C_{10})$heteroaryl. More preferably, $R^{15}$ is bromo, fluoro, —CN or oxadiazolyl, preferably [1,3,4] oxadiazol-2-yl.

In another preferred embodiment of the invention, G is $R^{15}$—$(CR^{16}R^{17})_p$—; wherein p is 0 or 1; $R^{15}$ is $R^{18}$; each of $R^{16}$ and $R^{17}$ is hydrogen; and $R^{18}$ is independently hydrogen or $(C_1-C_4)$alkyl; preferably methyl.

In another preferred embodiment of the invention, G is $R^{15}$—$(CR^{16}R^{17})_p$—; wherein p is 0 or 1; wherein G is oriented at a position para to the point of attachment of the Z ring to Y.

In another preferred embodiment of the invention, G is $R^{15}$—$(CR^{16}R^{17})_p$—; wherein p is 1; $R^{15}$ is $R^{19}$—(C=O)—(NR$^{21}$)—; each of $R^{16}$ or $R^{17}$ is independently hydrogen; $R^{19}$ is $(C_1-C_4)$alkyl, more preferably methyl, ethyl, or butyl; or $(C_3-C_8)$cycloalkyl, more preferably cyclobutyl; and $R^{21}$ is hydrogen.

In another preferred embodiment of the invention, G is $R^{15}$—$(CR^{16}R^{17})_p$—; wherein p is 1; $R^{15}$ is $(C_1-C_{10})$ heteroaryl, such as 2-pyrazolyl; and wherein each of $R^{16}$ and $R^{17}$ is independently hydrogen.

In another preferred embodiment of the invention, the heterocyclic ring "A" has the formula a) or b):

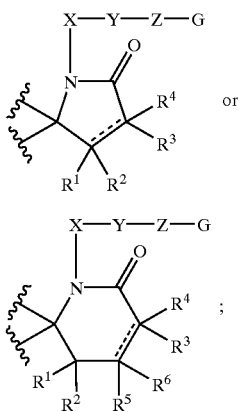

a)

b)

wherein X is $(C_1-C_{10})$heteroaryl selected from the group consisting of pyrazinyl, pyridazinyl, pyridyl and pyrimidinyl; more preferably X is pyridinyl; and Y is selected from the group consisting of a bond, oxygen, sulfur, —$CH_2$—, >$SO_2$, —$OCH_2$— and —$CH_2O$—; more preferably Y is oxygen, —$OCH_2$— or —$CH_2O$—; most preferably Y is oxygen.

Other preferred compounds of the invention include compounds of formula I, wherein the heterocyclic ring "A" has the formula a) or b), as defined above; X is $(C_1-C_{10})$ heteroaryl selected from the group consisting of pyrazinyl, pyridazinyl, pyridyl and pyrimidinyl; more preferably X is pyridinyl; most preferably wherein the pyridinyl together with the "A" ring and the group Y-Z-G has the formula:

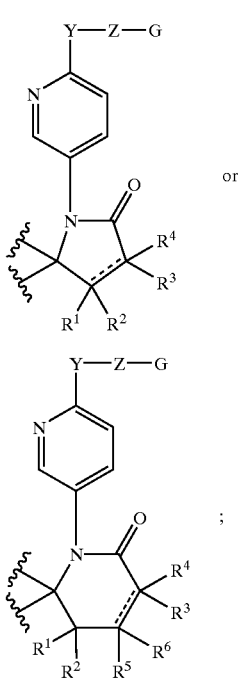

a")

or b")

wherein Y is a bond, oxygen, sulfur, —$CH_2$—, >$SO_2$, —$OCH_2$— or —$CH_2O$—; preferably Y is oxygen, —$OCH_2$— or —$CH_2O$—; more preferably Y is oxygen.

Other preferred compounds of the invention include compounds of formula I, wherein the heterocyclic ring "A" has the formula a) or b), as defined above; X is pyridinyl, most preferably wherein the pyridinyl together with the "A" ring and the group Y-Z-G has the formula a") or b") as defined above; Y is oxygen; Z is $(C_6-C_{10})$aryl, preferably phenyl; G is $R^{15}$—$(CR^{16}R^{17})_p$—; wherein p is 1; $R^{15}$ is $(C_1-C_{10})$ heteroaryl, such as 2-pyrazolyl; each of $R^{16}$ and $R^{17}$ is independently hydrogen or $(C_1-C_4)$alkyl, such as methyl, preferably hydrogen; and wherein G is oriented at a position para to the point of attachment of the Z ring to Y.

Most preferred compounds of the invention include compounds of formula I, wherein the heterocyclic ring "A" has the formula a) or b), as defined above; X is pyridinyl, most preferably wherein the pyridinyl together with the "A" ring and the group Y-Z-G has the formula a") or b") as defined above; Y is oxygen; Z is $(C_6-C_{10})$aryl, preferably phenyl; G is $R^{15}$—$(CR^{16}R^{17})_p$—; wherein p is 0; $R^{15}$ is selected from the group consisting of hydrogen, —CN, halo and oxadiazolyl; and wherein G is oriented at a position para to the point of attachment of the Z ring to Y.

Other most preferred compounds of the invention include compounds of formula I, wherein the heterocyclic ring "A" has the formula a) or b), as defined above; X is pyridinyl, most preferably wherein the pyridinyl together with the "A" ring and the group Y-Z-G has the formula a") or b") as defined above; Y is oxygen; Z is $(C_6-C_{10})$aryl, preferably phenyl; G is $R^{15}$—$(CR^{16}R^{17})_p$—; wherein p is 1; $R^{15}$ is $R^{19}$—(C=O)—(NR$^{21}$)—; each of $R^{16}$ and $R^{17}$ is independently hydrogen; $R^{19}$ is selected from the group consisting of $(C_1-C_4)$alkyl and $(C_3-C_8)$cycloalkyl, such as methyl, ethyl, propyl, butyl, or cyclobutyl; $R^{21}$ is selected from the group consisting of hydrogen or $(C_1-C_4)$alkyl; and wherein G is oriented at a position para to the point of attachment of the Z ring to Y.

Other compounds of the invention are selected from the group consisting of:

1-[6-(4-[1,3,4]Oxadiazol-2-yl-phenoxy)-pyridin-3-yl]-1,8,10-triaza-spiro[5.5]undecane-2,7,9,11-tetraone;

1-[6-(4-[1,3,4]Oxadiazol-2-yl-phenoxy)-pyridin-3-yl]-1,3,7,9-tetraaza-spiro[4.5]decane-2,6,8,10-tetraone;

1-[6-(4-[1,3,4]Oxadiazol-2-yl-phenoxy)-pyridin-3-yl]-1,3,8,10-tetraaza-spiro[5.5]undecane-2,7,9,11-tetraone;

4-[6-(4-[1,3,4]Oxadiazol-2-yl-phenoxy)-pyridin-3-yl]-1,1-dioxo-1λ$^6$-thia-2,4,7,9-tetraaza-spiro[4.5]decane-3,6,8,10-tetraone;

1-[6-(4-[1,3,4]Oxadiazol-2-yl-phenoxy)-pyridin-3-yl]-1,3,7,9-tetraaza-spiro[4.5]decane-2,4,6,8,10-pentaone;

1-[6-(4-[1,3,4]Oxadiazol-2-yl-phenoxy)-pyridin-3-yl]-2,2-dioxo-2λ$^6$-thia-1,7,9-triaza-spiro[4.5]decane-6,8,10-trione;

1-[6-(4-[1,3,4]Oxadiazol-2-yl-phenoxy)-pyridin-3-yl]-2,2-dioxo-2λ$^6$-thia-1,8,10-triaza-spiro[5.5]undecane-7,9,11-trione;

1-[6-(4-[1,3,4]Oxadiazol-2-yl-phenoxy)-pyridin-3-yl]-1,7,9-triaza-spiro[4.5]decane-6,8,10-trione;

1-[6-(4-Cyclobutylmethoxymethyl-phenoxy)-pyridin-3-yl]-1,7,9-triaza-spiro[4.5]decane-2,6,8,10-tetraone;

1-{6-[4-(2-Oxo-pyrrolidin-1-ylmethyl)-phenoxy]-pyridin-3-yl}-1,7,9-triaza-spiro[4.5]decane-2,6,8,10-tetraone;

1-[6-(1H-indazol-5-yloxy)-pyridin-3-yl]-1,7,9-triaza-spiro[4.5]decane-2,6,8,10-tetraone;

1-[6-(4-Fluoro-phenoxy)-pyridin-3-yl]-3-methyl-1,7,9-triaza-spiro[4.5]decane-2,6,8,10-tetraone;

1-[6-(3-Fluoro-phenoxy)-pyridin-3-yl]-1,7,9-triaza-spiro[4.5]decane-2,6,8,10-tetraone;

4-[5-(2,7,9,11-Tetraoxo-1,8,10-triaza-spiro[-5.5]undec-1-yl)-pyridin-2-yloxy]-benzonitrile;

1-[6-(4-Ethyl-phenoxy)-pyridin-3-yl]-1,8,10-triaza-spiro[5.5]undecane-2,7,9,11-tetraone;

N-{4-[5-(2,7,9,11-Tetraoxo-1,8,10-triaza-spiro[5.5]undec-1-yl)-pyridin-2-yloxy]-benzyl}-acetamide;
Azetidine-1-carboxylic acid 4-[5-(2,7,9,11-tetraoxo-1,8,10-triaza-spiro[5.5]undec-1-yl)-pyridin-2-yloxy]-benzylamide;
1-[6-(4-Pyrazol-1-ylmethyl-phenoxy)-pyridin-3-yl]-1,8,10-triaza-spiro[5.5]undecane-2,7,9,11-tetraone;
1-[6-(4-Fluoro-phenoxy)-pyridin-3-yl]-1,8,10-triaza-spiro[5.5]undecane-2,7,9,11-tetraone;
1-[6-(4-Fluoro-phenoxy)-pyridin-3-yl]-1,3,7,9-tetraaza-spiro[4.5]decane-2,6,8,10-tetraone;
1-[6-(4-Ethyl-phenoxy)-pyridin-3-yl]-1,3,7,9-tetraaza-spiro[4.5]decane-2,6,8,10-tetraone;
4-[5-(2,6,8,10-Tetraoxo-1,3,7,9-tetraaza-spiro[4.5]dec-1-yl)-pyridin-2-yloxy]-benzonitrile;
N-{4-[5-(2,6,8,10-Tetraoxo-1,3,7,9-tetraaza-spiro[4.5]dec-1-yl)-pyridin-2-yloxy]-benzyl}-acetamide;
Azetidine-1-carboxylic acid 4-[5-(2,6,8,10-tetraoxo-1,3,7,9-tetraaza-spiro[4.5]dec-1-yl)-pyridin-2-yloxy]-benzylamide;
1-[6-(4-Pyrazol-1-ylmethyl-phenoxy)-pyridin-3-yl]-1,3,7,9-tetraaza-spiro[4.5]decane-2,6,8,10-tetraone;
1-[6-(4-Fluoro-phenoxy)-pyridin-3-yl]-1,3,8,10-tetraaza-spiro[5.5]undecane-2,7,9,11-tetraone;
1-[6-(4-Ethyl-phenoxy)-pyridin-3-yl]-1,3,8,10-tetraaza-spiro[5.5]undecane-2,7,9,11-tetraone;
4-[5-(2,7,9,11-Tetraoxo-1,3,8,10-tetraaza-spiro[5.5]undec-1-yl)-pyridin-2-yloxy]-benzonitrile;
N-{4-[5-(2,7,9,11-Tetraoxo-1,3,8,10-tetraaza-spiro[5.5]undec-1-yl)-pyridin-2-yloxy]-benzyl}-acetamide;
Azetidine-1-carboxylic acid 4-[5-(2,7,9,11-tetraoxo-1,3,8,10-tetraaza-spiro[5.5]undec-1-yl)-pyridin-2-yloxy]-benzylamide;
1-[6-(4-Pyrazol-1-ylmethyl-phenoxy)-pyridin-3-yl]-1,3,8,10-tetraaza-spiro[5.5]undecane-2,7,9,11-tetraone;
4-[6-(4-Fluoro-phenoxy)-pyridin-3-yl]-1,1-dioxo-1$\lambda^8$-thia-2,4,7,9-tetraaza-spiro[4.5]decane-3,6,8,10-tetraone;
4-[6-(4-Ethyl-phenoxy)-pyridin-3-yl]-1,1-dioxo-1$\lambda^6$-thia-2,4,7,9-tetraaza-spiro[4.5]decane-3,6,8,10-tetraone;
4-[5-(1,1,3,6,8,10-Hexaoxo-1$\lambda^6$-thia-2,4,7,9-tetraaza-spiro[4.5]dec-4-yl)-pyridin-2-yloxy]-benzonitrile;
N-{4-[5-(1,1,3,6,8,10-Hexaoxo-1$\lambda^6$-thia-2,4,7,9-tetraaza-spiro[4.5]dec-4-yl)-pyridin-2-yloxy]-benzyl}-acetamide;
Azetidine-1-carboxylic acid 4-[5-(1,1,3,6,8,10-hexaoxo-1$\lambda^6$-thia-2,4,7,9-tetraaza-spiro[4.5]dec-4-yl)-pyridin-2-yloxy]-benzylamide;
1,1-Dioxo-4-[6-(4-pyrazol-1-ylmethyl-phenoxy)-pyridin-3-yl]-1$\lambda^6$-thia-2,4,7,9-tetraaza-spiro[4.5]decane-3,6,8,10-tetraone;
1-[6-(4-Fluoro-phenoxy)-pyridin-3-yl]-1,3,7,9-tetraaza-spiro[4.5]decane-2,4,6,8,10-pentaone;
4-[5-(2,4,6,8,10-Pentaoxo-1,3,7,9-tetraaza-spiro[4.5]dec-1-yl)-pyridin-2-yloxy]-benzonitrile;
N-{4-[5-(2,4,6,8,10-Pentaoxo-1,3,7,9-tetraaza-spiro[4.5]dec-1-yl)-pyridin-2-yloxy]-benzyl}-acetamide;
Azetidine-1-carboxylic acid 4-[5-(2,4,6,8,10-pentaoxo-1,3,7,9-tetraaza-spiro[4.5]dec-1-yl)-pyridin-2-yloxy]-benzylamide;
1-[6-(4-Pyrazol-1-ylmethyl-phenoxy)-pyridin-3-yl]-1,3,7,9-tetraaza-spiro[4.5]decane-2,4,6,8,10-pentaone;
1-[6-(4-Ethyl-phenoxy)-pyridin-3-yl]-1,3,7,9-tetraaza-spiro[4.5]decane-2,4,6,8,10-pentaone;
1-[6-(4-Fluoro-phenoxy)-pyridin-3-yl]-2,2-dioxo-2$\lambda^6$-thia-1,7,9-triaza-spiro[4.5]decane-6,8,10-trione;
1-[6-(4-Ethyl-phenoxy)-pyridin-3-yl]-2,2-dioxo-2$\lambda^6$-thia-1,7,9-triaza-spiro[4.5]decane-6,8,10-trione;
4-[5-(2,2,6,8,10-Pentaoxo-2$\lambda^6$-thia-1,7,9-triaza-spiro[4.5]dec-1-yl)-pyridin-2-yloxy]-benzonitrile;
N-{4-[5-(2,2,6,8,10-Pentaoxo-2$\lambda^6$-thia-1,7,9-triaza-spiro[4.5]dec-1-yl)-pyridin-2-yloxy]-benzyl}-acetamide;
Azetidine-1-carboxylic acid 4-[5-(2,2,6,8,10-pentaoxo-2$\lambda^6$-thia-1,7,9-triaza-spiro[4.5]dec-1-yl)-pyridin-2-yloxy]-benzylamide;
2,2-Dioxo-1-[6-(4-pyrazol-1-ylmethyl-phenoxy)-pyridin-3-yl]-2$\lambda^6$-thia-1,7,9-triza-spiro[4.5]decane-6,8,10-trione;
1-[6-(4-Fluoro-phenoxy)-pyridin-3-yl]-2,2-dioxo-2$\lambda^6$-thia-1,8,10-triaza-spiro[5.5]undecane-7,9,11-trione;
1-[6-(4-Ethyl-phenoxy)-pyridin-3-yl]-2,2-dioxo-2$\lambda^6$-thia-1,8,10-triaza-spiro[5.5]undecane-7,9,11-trione;
4-[5-(2,2,7,9,11-Pentaoxo-2$\lambda^6$-thia-1,8,10-triaza-spiro[5.5]undec-1-yl)-pyridin-2-yloxy]-benzonitrile;
N-{4-[5-(2,2,7,9,11-Pentaoxo-2$\lambda^6$-thia-1,8,10-triaza-spiro[5.5]undec-1-yl)-pyridin-2-yloxy]-benzyl}-acetamide;
Azetidine-1-carboxylic acid 4-[5-(2,2,7,9,11-pentaoxo-2$\lambda^6$-thia-1,8,10-triaza-spiro[5.5]undec-1-yl)-pyridin-2-yloxy]-benzylamide;
2,2-Dioxo-1-[6-(4-pyrazol-1-ylmethyl-phenoxy)-pyridin-3-yl]-2$\lambda^6$-thia-1,8,10-triaza-spiro[5.5]undecane-7,9,11-trione;
1-[6-(4-Ethyl-phenoxy)-pyridin-3-yl]-1,7,9-triaza-spiro[4.5]decane-6,8,10-trione;
1-[6-(4-Fluoro-phenoxy)-pyridin-3-yl]-1,7,9-triaza-spiro[4.5]decane-6,8,10-trione;
4-[5-(6,8,10-Trioxo-1,7,9-triaza-spiro[4.5]dec-1-yl)-pyridin-2-yloxy]-benzonitrile;
N-{4-[5-(6,8,10-Trioxo-1,7,9-triaza-spiro[4.5]dec-1-yl)-pyridin-2-yloxy]-benzyl}-acetamide;
Azetidine-1-carboxylic acid 4-[5-(6,8,10-trioxo-1,7,9-triaza-spiro[4.5]dec-1-yl)-pyridin-2-yloxy]-benzylamide;
1-[6-(4-Pyrazol-1-ylmethyl-phenoxy)-pyridin-3-yl]-1,7,9-triaza-spiro[4.5]decane-6,8,10-trione;
1-[6-(3-Fluoro-4-[1,3,4]oxadiazol-2-yl-phenoxy)-pyridin-3-yl]-1,8,10-triaza-spiro[5.5]undecane-2,7,9,11-tetraone;
1-[6-(2-Fluoro-4-[1,3,4]oxadiazol-2-yl-phenoxy)-pyridin-3-yl]-1,8,10-triaza-spiro[5.5]undecane-2,7,9,11-tetraone;
1-[6-(3-Methyl-4-[1,3,4]oxadiazol-2-yl-phenoxy)-pyridin-3-yl]-1,8,10-triaza-spiro[5.5]undecane-2,7,9,11-tetraone;
1-[4-(4-[1,3,4]Oxadiazol-2-yl-phenyl)-phenyl]-1,8,10-triaza-spiro[5.5]undecane-2,7,9,11-tetraone;
1-[6-(Pyridin-4-yloxy)-pyridin-3-yl]-1,8,10-triaza-spiro[5.5]undecane-2,7,9,11-tetraone;
1-[5-(Pyridin-4-yloxy)-pyridin-2-yl]-1,8,10-triaza-spiro[5.5]undecane-2,7,9,11-tetraone;
1-[4-(Pyridin-4-yloxy)-phenyl]-1,8,10-triaza-spiro[5.5]undecane-2,7,9,11-tetraone; 1-[4-(Pyridin-4-yloxy)-phenyl]-1,7,9-triaza-spiro[4.5]decane-2,6,8,10-tetraone;
Azetidine-1-carboxylic acid 4-[5-(2,6,8,10-tetraoxo-1,7,9-triaza-spiro[4.5]dec-1-yl)-pyridin-2-yloxy]-benzylamide; and the pharmaceutically acceptable salts thereof.

Specific preferred compounds of formula I are selected from the group consisting of:

1-[6-(4-Fluoro-phenoxy)-pyridin-3-yl]-1,7,9-triaza-spiro[4.5]decane-2,6,8,10-tetraone;
1-[6-(4-Fluoro-phenoxy)-pyridin-3-yl]-1,8,10-triaza-spiro[5.5]undecane-2,7,9,11-tetraone;
4-[5-(2,6,8,10-Tetraoxo-1,7,9-triaza-spiro[4.5]dec-1-yl)-pyridin-2-yloxy]-benzonitrile;
1-[6-(4-[1,3,4]oxadiazol-2-yl-phenoxy)-pyridin-3-yl]-1,7,9-triaza-spiro[4.5]decane-2,6,8,10-tetraone;
1-[6-(4-Ethyl-phenoxy)-pyridin-3-yl]-1,7,9-triaza-spiro[4.5]decane-2,6,8,10-tetraone;
N-{4-[5-(2,6,8,10-Tetraoxo-1,7,9-triaza-spiro[4.5]dec-1-yl)-pyridin-2-yloxy]-benzyl}-acetamide;

N-{4-[5-(2,6,8,10-Tetraoxo-1,7,9-triaza-spiro[4.5]dec-1-yl)-pyridin-2-yloxy]-benzyl}-propionamide;
N-{4-[5-(2,6,8,10-Tetraoxo-1,7,9-triaza-spiro[4.5]dec-1-yl)-pyridin-2-yloxy]-benzyl}-butyramide;
Pentanoic acid 4-[5-(2,6,8,10-tetraoxo-1,7,9-triaza-spiro[4.5]dec-1-yl)-pyridin-2-yloxy]-benzylamide;
Cyclobutanecarboxylic acid 4-[5-(2,6,8,10-tetraoxo-1,7,9-triaza-spiro[4.5]dec-1-yl)-pyridin-2-yloxy]-benzylamide;
1-[6-(4-Bromo-phenoxy)-pyridin-3-yl]-1,7,9-triaza-spiro[4.5]decane-2,6,8,10-tetraone;
1-[6-(4-pyrazol-1-ylmethyl-phenoxy)-pyridin-3-yl]-1,7,9-triaza-spiro[4.5]decane-2,6,8,10-tetraone;

and the pharmaceutically acceptable salts thereof.

The present invention also relates to a pharmaceutical composition for the treatment of a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by metalloproteinase activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of matrix metalloproteinases or other metalloproteinases involved in matrix degradation, in a mammal, including a human, comprising an effective amount of a compound of formula I or a pharmaceutically acceptable salt thereof.

The present invention also relates to a method for treating a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by matrix metalloproteinase activity in a mammal, including a human, comprising administering to said mammal an amount of a compound of formula I or a pharmaceutically acceptable salt thereof effective in treating such a condition.

The present invention also relates to a method for the inhibition of matrix metalloproteinases or other metalloproteinases involved in matrix degradation, in a mammal, including a human, comprising administering to said mammal an effective amount of a compound of formula I or a pharmaceutically acceptable salt thereof.

The present inventors have also discovered that it is possible to identify inhibitors of formula I with differential metalloprotease activity (preferably MMP-13 inhibitory activity). One group of preferred inhibitors of formula I the inventors have been able to identify include those which selectively inhibit MMP-13 preferentially over MMP-1. The compounds of the invention also possess selectivity over a related group of enzymes known as reprolysins, such as TACE and aggrecanase. Another group of preferred inhibitors of formula I the inventors have been able to identify include those which selectively inhibit MMP-13 preferentially over MMP-1 and MMP-14. Another group of preferred inhibitors of formula I the inventors have been able to identify include those which selectively inhibit MMP-13 preferentially over MMP-1 and 12. Another group of preferred inhibitors of formula I the inventors have been able to identify include those which selectively inhibit MMP-13 preferentially over MMP-1, 12 and 14. Another group of preferred inhibitors of formula I the inventors have been able to identify include those which selectively inhibit MMP-13 preferentially over MMP-1, 2, 3, 7, 9 and 14. Most preferred compounds of the invention selectively inhibit MMP-13 preferentially over MMP-1, 2, 3, 7, 9, 12 and 14 and mammalian reprolysins.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Connective tissue disorders" as used herein refers to disorders such as degenerative cartilage loss following traumatic joint injury, osteoarthritis, osteoporosis, Paget's disease, loosening of artificial joint implants, periodontal disease and gingivitis.

"Destruction of articular cartilage" as used herein refers to connective tissue disorders resulting in articular cartilage destruction, preferably joint injury, reactive arthritis, acute pyrophosphate arthritis (pseudogout), psoriatic arthritis, or juvenile rheumatoid arthritis, more preferably osteoarthritis.

"Inflammatory disorders" as used herein refers to disorders such as rheumatoid arthritis, ankylosing spondylitis, psoriatic arthritis, psoriasis, chondrocalcinosis, gout, inflammatory bowel disease, ulcerative colitis, Crohn's disease and cachexia.

"Immunology/allergy disorders" as used herein refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein refers to disorders such as septic arthritis, AIDS, fever; Prion diseases, myasthenia gravis, Malaria, sepsis, hemodynamic shock and septic shock.

"Respiratory diseases" as used herein refers to disorders such as chronic obstructive pulmonary disease (including emphysema), acute respiratory distress syndrome, asthma, hyperoxic alveolar injury and idiopathic pulmonary fibrosis and other fibrotic lung diseases.

"Cardiovascular diseases" as used herein refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases" as used herein refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including "Age Related Macular Degeneration (ARMD) including both wet and dry forms), proliferative vitreoretinopathy and retinopathy of prematurity.

"Metabolic diseases" as used herein refers to disorders such as diabetes (including non-insulin dependent diabetes mellitus, diabetic retinopathy, insulin resistance, diabetic ulceration).

"Central Nervous System" (CNS) disorders as used herein refers to disorders such as head trauma, spinal cord injury, Inflammatory diseases of the central nervous system, neurodegenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases" as used herein refers to disorders such as nephrotic syndromes such as glomerulonephritis and glomerular disease of the kidney, proteinuria, cirrhosis of the liver and interstitial nephritis.

"Reproductive Health disorders" as used herein refers to disorders such as endometriosis, contraception (male/female), dysmenorrhea, dysfunctional uterine bleeding, premature rupture of fetal membranes and abortifactant.

"Gastric disorders" as used herein refers to disorders such as colonic anastomosis and gastric ulcers.

"Skin disorders" as used herein refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers" as used herein refers to disorders such as solid tumor cancer including colon cancer, breast cancer, lung cancer and prostrate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney and other urinary tissues, eye brain and central nervous system, thyroid and other endocrine gland, Hodgkin's disease, non-Hodgkin's lymphomas, multiple myeloma and hematopoietic malignancies including leukemias and lymphomas including lymphocytic, granulocytic and monocytic.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

This invention also encompasses pharmaceutical compositions containing prodrugs of compounds of the formula I.

This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently, bonded to the above substituents of formula I through the carbonyl carbon prodrug sidechain. Prodrugs also include dimers of compounds of formula I.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as infliximab, D2E7 and CDP-870) and TNF receptor immunoglobulin molecules (such as etanercept), ICE inhibitors, MEKK1 inhibitors, COX-2 inhibitors such as celecoxib, rofecoxib, valdecoxib and etoricoxib; low dose methotrexate, lefunimide, steroids, glucosamines, chondrosamines/ sulfates, gabapentin, A-agonists, IL-1 process and release inhibitors, IL-1 receptor antagonists such as Kineret®, CCR-1 antagonists, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib, etoricoxib and rofecoxib, analgesics, steroids, glucosamines, chondrosamines/ sulfates, gabapentin, A-agonists, IL-1 process and release inhibitors, CCR-1 antagonists, LTD-4, LTB-4 and 5-LO inhibitors, p38 kinase inhibitors and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, paclitaxel, docetaxel and alkaloids, such as vincristine and antimetabolites such as methotrexate.

The compounds of the present invention may also be used in combination with cardiovascular agents such as calcium channel blockers (such as amlodipine and nifedipine), lipid lowering agents such as statins (such as lovastatin, atorvastatin, pravastatin and simvastatin), adrenergics such as doxazosin and terazosin; fibrates, beta-blockers, Ace inhibitors (such as captopril, lisinopril, fosinopril, enalapril and quinapril), Angiotensin-2 receptor antagonists such as losartan and irbesartan; nitrates, CCB's, diuretics such as digitalis and platelet aggregation inhibitors. The compounds of the present invention may also be used in combination with plaque rupture preventitive agents such as statins, zithromax, NSAIDs including aspirin, heparin, urarfarin, abciximab, TPA and platelet Inhibitors. The compounds of the present invention may also be used in combination with stroke treatment agents such as NIF, NHEI's and CCRIR antagonists.

The compounds of the present invention may also be used in combination with CNS agents such as antidepressants (such as sertraline), anti-Parkinsonian drugs (such as deprenyl, carbadopa, L-dopa, dopamine receptor agonists such as ropinirole, pergolide and pramipexole; MAOB inhibitors such as selegiline and rasagiline, catechol-O-methyltrasferase inhibitors such as tolcapone, A-2 inhibitors, dopamine reuptake inhibitors, NMDA antagonists, Nicotine agonists, NK-1 inhibitors, dopamine agonists and inhibitors of neuronal nitric oxide synthase) and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

The compounds of the present invention may also be used in combination with agents for the treatment of respiratory diseases such as PDE-IV inhibitors, steroidals such as fluticasone, triamcinolone, budesonide, budesonide and beclomethasone, anticholinergics such as ipratropium, sympathomimetics such as salmeterol, albuterol and Xopenex, decongestants such as fexofenadine, loratadine and cetirizine; leukotriene antagonists such as zafirlukast and motelukast; and mast cell stabilizers such as zileuton.

The compounds of the present invention may also be used in combination with agents for the treatment of skin disorders such as tretinoin, isotretinoin, steroids such as cortisone and mometasone, antibiotics such as tetracycline, antifungals such as clotrimazole, miconazole and fluconazole and PDE-IV inhibitors.

The compounds of the present invention may also be used in combination with agents for the treatment of diabetes such as insulin, including human or humanized insulin and inhaled insulin, aldose reductase inhibitors, sorbitol dehydrogenase inhibitors, antidiabetic agents such as biguanides such as metformin; glitazones, glycosidase inhibitors such as acarbose, sulfonylureas such as glimepiride and glipizide; and thiazolidinediones such as pioglitazone, rosiglitazone and trogliazone. Preferred combinations are useful for treating the side effects of diabetes such as retinopathy, nephropathy and neuropathy, preferably retinopathy.

DETAILED DESCRIPTION OF THE INVENTION

The following reaction Schemes illustrate the preparation of the compounds of the present invention. Unless otherwise indicated each of X, Y, Z, G, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ in the reaction Schemes and the discussion that follows is defined as above.

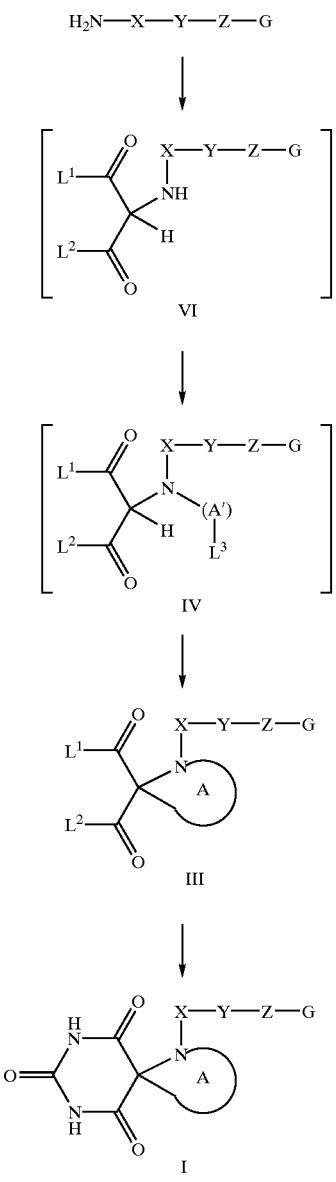

SCHEME 1

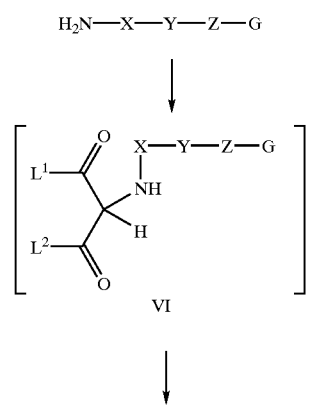

SCHEME 2

-continued
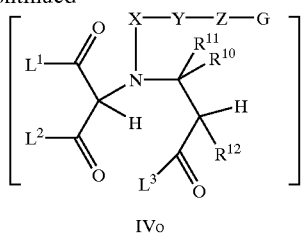
IVo
↓
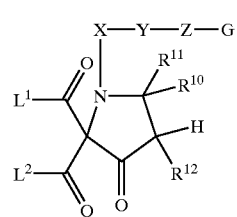
IIIo
↓
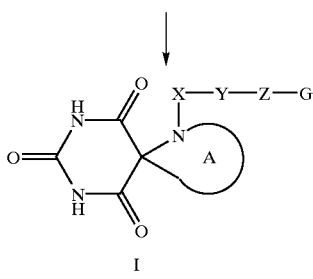
I
SCHEME 3
NO₂—X—L⁷    X
↓
NO₂—X—Y—Z—G    VIII
↓
H₂N—X—Y—Z—G
Scheme 1 refers to the preparation of compounds of the formula I. Referring to Scheme 1, compounds of formula I, wherein the heterocyclic ring "A" has the formulae a–n (i.e., a compound of the formulae Ia–In, respectively):
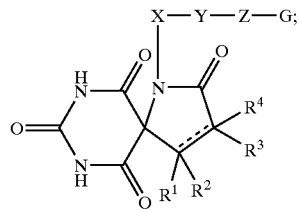
Ia
-continued
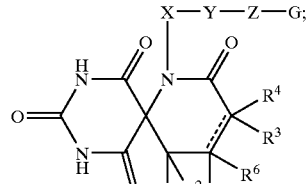
Ib
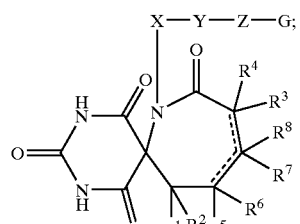
Ic
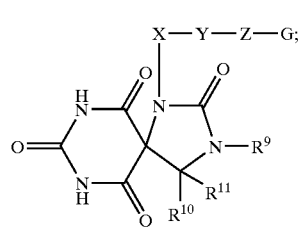
Id
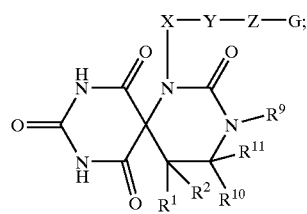
Ie
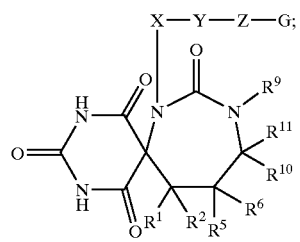
If
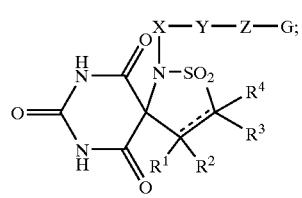
Ig
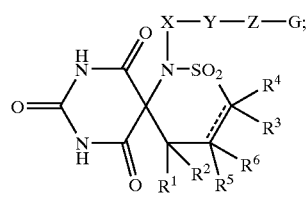
Ih can be prepared by reacting a compound of the formulae IIIa–IIIn, respectively:

IIIh 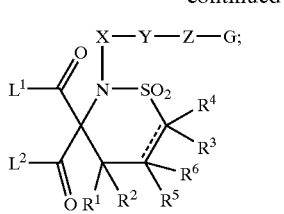

IIIi 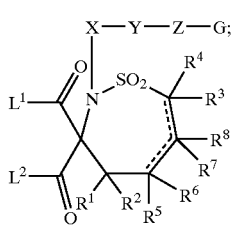

IIIj 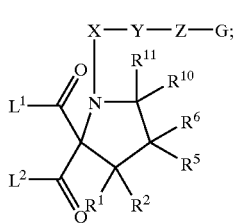

IIIk 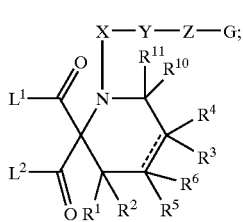

IIIl 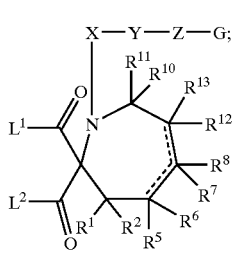

IIIm 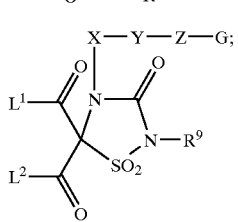

and

IIIn 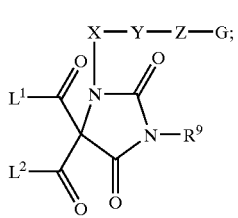

wherein $L^1$ and $L^2$ are leaving groups such as alkoxy, preferably methoxy, ethoxy or benzyloxy, more preferably methoxy or ethoxy, with a urea of formula II (i.e., $H_2N$—(CO)—$NH_2$) in the presence of a suitable base in a polar solvent. Suitable bases include alkoxide bases, such as sodium methoxide, sodium ethoxide, or potassium tert-butoxide, preferably sodium ethoxide. Suitable solvents include tetrahydrofuran, dimethylformamide, or alcohols (such as ethanol), preferably tetrahydrofuran or dimethylformamide. The aforesaid reaction is conducted at a temperature of about 20° C. to about 90° C., preferably about 50° C. to about 80° C., for a time period of about 5 minutes to about 8 hours.

A compound of formulae IIIa–IIIl, respectively, can be prepared by reacting a compound of formulae IVa–IVl, respectively:

IVa 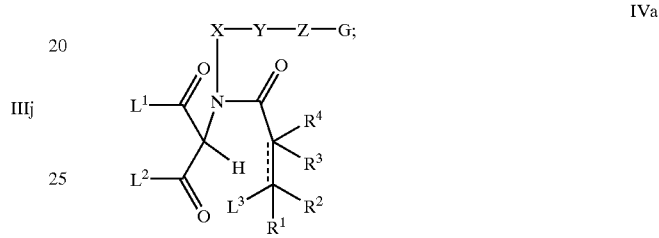

IVb 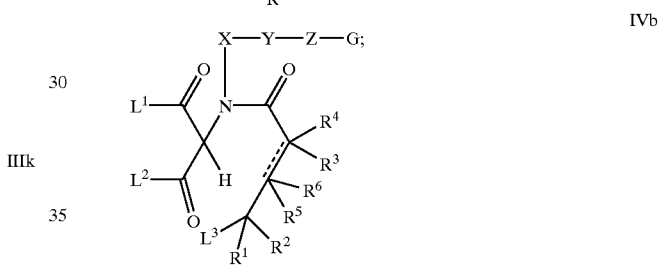

IVc 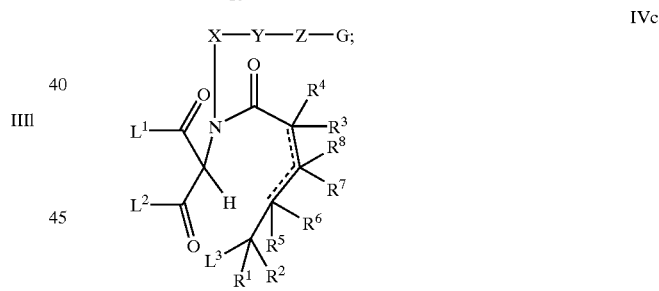

IVd 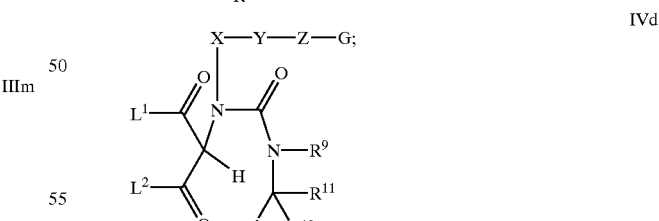

IVe 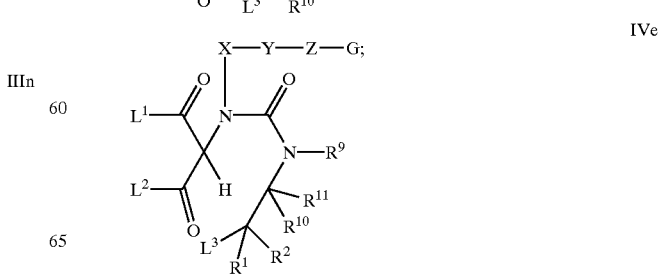

IVf
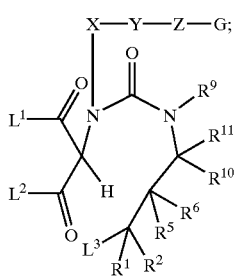

IVg
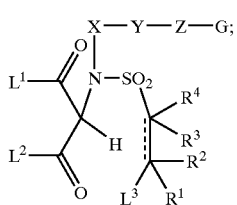

IVh
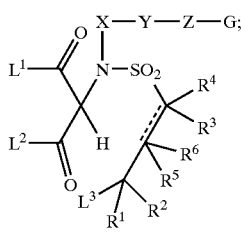

IVi
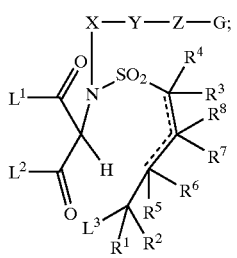

IVj
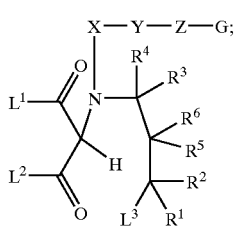

IVk
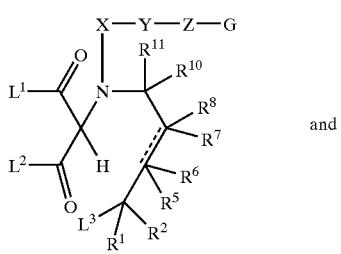
and

IVl
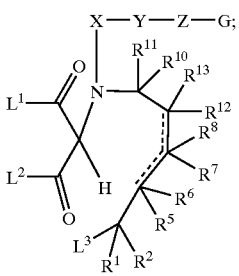

wherein $L^1$ and $L^2$ are leaving groups such as alkoxy, preferably methoxy, ethoxy or benzyloxy, more preferably methoxy or ethoxy and wherein $L^3$ is a suitable leaving group, such as halo, para-tolylsulfonyloxy (OTs), or methylsulfonyloxy (OMs), preferably halo, such as bromo or iodo, with a suitable base in a polar solvent. Suitable bases include tertiary amines, such as triethylamine. Other suitable bases include a strongly basic macro-reticular resin or gel type resin, such as Amberlyst 400® resin (hydroxide form). Suitable solvents include alcoholic solvents, preferably ethanol. The aforesaid reaction can be conducted at a temperature of about −10° C. to about 50° C., preferably about 20° C., for a period of about 6 to about 36 hours.

A compound of formulae IIIm–IIIn, respectively, can be prepared by reacting a compound of formulae IVm–IVn, respectively:

IVm
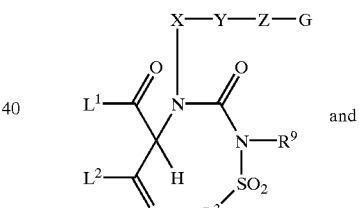
and

IVn
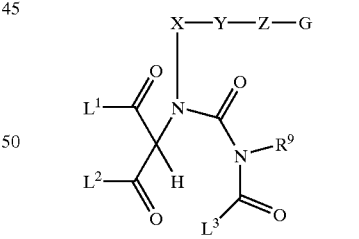

wherein $L^3$ is a suitable leaving group, with a suitable base in a polar solvent according to methods analogous to the preparation of the compounds of formulae IIIa–IIIi in the foregoing paragraph. Suitable leaving groups of the formula $L^3$ include halo, para-tolylsulfonyloxy (OTs), or methylsulfonyloxy (OMs). Preferably $L^3$ is halo, such as chloro. The aforesaid reaction can be conducted at a temperature of about 0° C. to about 50° C., preferably about 20° C., for a period of about 1 hour to about 4 hours. Suitable solvents include tetrahydrofuran, dimethylformamide and alcohol.

A compound of formulae IVa–IVi, respectively, can be prepared by reacting a compound of formula VI with a compound of general formula $$L^3\text{-}(A')\text{-}L^4 \qquad (V)$$

(i.e., a compound of formulae Va–Vi, respectively):

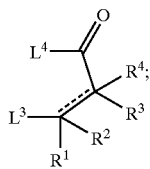
Va

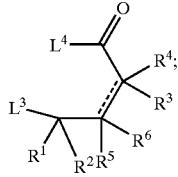
Vb

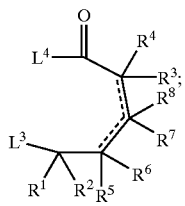
Vc

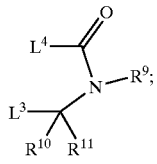
Vd

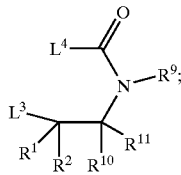
Ve

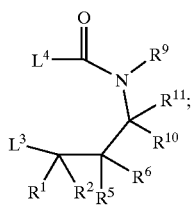
Vf

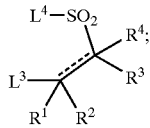
Vg

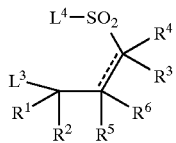
and
Vh

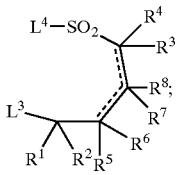
Vi wherein each of $L^3$ and $L^4$ is a suitable leaving group, such as halo, para-tolylsulfonyloxy (OTs), or methylsulfonyloxy (OMs). Preferably $L^3$ is halo, such as bromo, chloro or iodo. Preferably $L^4$ is chloro or fluoro. Optionally, the aforementioned reaction may be conducted in the presence of a tertiary amine base, such as N,N-dimethylaniline or pyridine, in the presence of a suitable solvent, such as a hydrocarbon solvent (benzene or toluene), tetrahydrofuran or methylene chloride. The aforementioned reaction is conducted at a temperature of about 20° C. to about 90° C., preferably about 50° C. to about 80° C., for a time period of about 30 minutes to about 6 hours.

Preferably, the aforementioned reaction is conducted in an aromatic hydrocarbon solvent, such as benzene or toluene, in the absence of the aforementioned base.

A compound of formulae IVj–IVl, respectively, can be prepared by reacting a compound of formula VI with a compound of formula:

$$L^3\text{-}(A')\text{-}L^4 \qquad (V)$$

(i.e., a compound of formulae Vj–Vl, respectively):

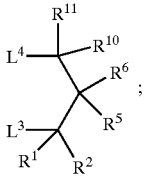
Vj

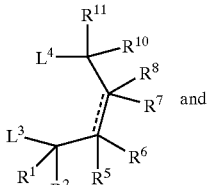
and
Vk

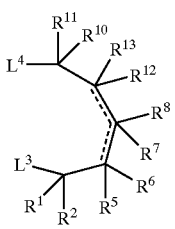
Vl wherein each of $L^3$ and $L^4$ is a suitable leaving group, such as halo, para-tolylsulfonyloxy (OTs) or methylsulfonyloxy (OMs), according to the methods analogous to those described in the preparation of the compounds of formulae IVa–IVi in the foregoing paragraph. Preferably $L^3$ is chloro, bromo, or iodo. Preferably $L^4$ is chloro, bromo, or iodo. The aforesaid reaction can be conducted at a temperature of about 0° C. to about 50° C., preferably about 20° C., for a time period of about 30 minutes to about 12 hours.

Compounds of formulae IVm–IVn, respectively, can be prepared by reacting a compound of formula VI with a compound of formula

L³-(A')-L⁴ (V)

(i.e., a compound of formulas Vm–Vn, respectively):

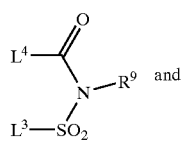
Vm

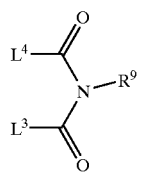
Vn wherein each of L³ and L⁴ is a suitable leaving group, such as halo, para-tolylsulfonyloxy (OTs) or methylsulfonyloxy (OMs), according to the methods analogous to those described in the preparation of the compounds of formulae IVa–IVi in the foregoing paragraph. Preferably L³ is halo, such as chloro. Preferably L⁴ is halo, such as chloro. The aforesaid reaction can be conducted at a temperature of about 0° C. to about 80° C., preferably about 0° C. to about 40° C., for a time period of about 30 minutes to about 8 hours.

Alternatively, compounds of formulae IVd, IVe and IVf, respectively, can be prepared by reacting a compound of formula VI with a compound of formula (A')-L³ (V)

(i.e., a compound of formulae Vd', Ve' and Vf', respectively):

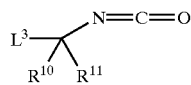
Vd'

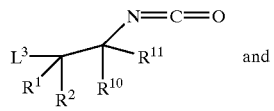
Ve'

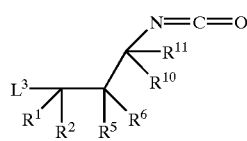
Vf' wherein L³ is preferably halo, most preferably chloro, bromo, or iodo. Optionally, the aforementioned reaction can be conducted in the presence of a tertiary amine base in a suitable solvent. Suitable bases include N,N-dimethylaniline or pyridine. Suitable solvents include hydrocarbon solvent (benzene or toluene), tetrahydrofuran, or methylene chloride, preferably aromatic hydrocarbon solvent, such as benzene or toluene. The aforementioned reaction is conducted at a temperature of about 20° C. to about 90° C., preferably about 50° C. to about 80° C., for a time period of about 30 minutes to about 6 hours. Preferably, the aforementioned reaction is conducted in the absence of any aforementioned base.

Alternatively, compounds of formulae IVm and IVn, respectively, can be prepared by reacting a compound of formula VI with a compound of formula (A')-L³ (V)

(i.e., a compound of formulae Vm' and Vn', respectively):

L³—SO₂—N=C=O and
Vm'

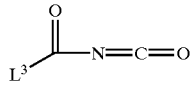
Vn' wherein L³ is preferably halo, most preferably chloro. The aforementioned reaction can be conducted optionally in the presence of a tertiary amine base in a suitable solvent. Suitable bases include N,N-dimethylaniline or pyridine. Suitable solvents include a hydrocarbon solvent (benzene or toluene), tetrahydrofuran or methylene chloride, preferably aromatic hydrocarbon solvent, such as benzene or toluene. The aforesaid reaction can be conducted at a temperature of about –10° C. to about 50° C., preferably about 0° C. to about 30° C., for a time period of about 30 minutes to about 12 hours. Preferably, the aforementioned reaction is conducted in the absence of any aforementioned base.

A compound of formula VI can be prepared by reacting a compound of formula $H_2N—X—Y-Z-G$ with a compound of the formula VII:

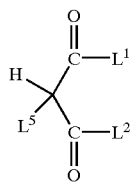
VII wherein L¹ and L² are leaving groups, such as methoxy, ethoxy, or benzyloxy; preferably ethoxy; and L⁵ is a leaving group, such as halo, para-tolylsulfonyloxy (OTs) or methylsulfonyloxy (OMs); preferably halo; most preferably chloro or bromo. The aforesaid reaction can be performed either neat or in the presence of a suitable solvent, preferably neat, or in the presence of a suitable base. Suitable solvents include tetrahydrofuran or dimethylformamide. Suitable bases include a weak tertiary amine base, preferably tertiary aniline bases, most preferably N,N-dimethylaniline. Preferably, the aforementioned reaction is conducted at a temperature of about 23° C. to about 100° C., preferably about 50° C. to about 90° C., for a time period of about 30 minutes to about 24 hours.

In the aforesaid reactions, each of the compounds of formulae IVj–IVl may be Isolated, but are preferably carried on to the next step without isolation. Thus, in Scheme 1, the compound of formulae IIIj–IIIl is preferably prepared in a one pot preparation from a compound of the formula VI.

If the compounds of the formulae IVj–IVl are not isolated, the suitable solvent for the one-pot preparation is dimethylformamide, tetrahydrofuran, or alcohols, preferably alcohols, such as ethanol. Preferably, the one-pot preparation is conducted in the presence of an alkoxide base, preferably sodium methoxide or sodium ethoxide. The aforesaid one pot preparation is conducted at a temperature of about 40° C. to about 90° C., preferably about 60° C. to about 80° C., for a time period of about 15 minutes to about 12 hours.

The compounds of formula H$_2$N—X—Y-Z-G are commercially available or can be made by methods well known to those skilled in the art. Alternatively, the compounds of formula H$_2$N—X—Y-Z-G can be prepared as described in Scheme 3.

A compound of the formula VII can be made by methods well known in the art such as those described in PCT Patent Publication WO 98/58925 or reviewed in *The Organic Chemistry of Drug Synthesis,* D. Lednicer and L. A. Mitscher, Volume 1, pages 167 to 277 and references therein. Each of the above referenced publications and applications is hereby incorporated by reference in its entirety.

Compounds of the formula II are commercially available or can be made by methods well known to those skilled in the art.

Scheme 2 refers to the preparation of a compound of the formula I, wherein the heterocyclic ring "A" has the formula o, i.e., a compound of formula Io. Referring to Scheme 2, a compound of formula Io:

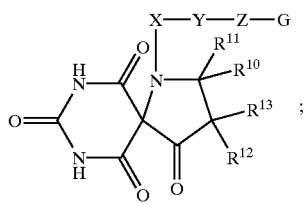

can be prepared by reacting a compound of the formula IIIo, wherein L$^1$ and L$^2$ are leaving groups, with a urea of formula II (i.e., H$_2$N—(CO)—NH$_2$) in the presence of a suitable base in a polar solvent. Suitable leaving groups include methoxy, ethoxy, or benzyloxy, preferably ethoxy. Suitable bases include alkoxide bases, such as sodium methoxide, sodium ethoxide and potassium tert-butoxide, preferably sodium ethoxide. Suitable solvents include tetrahydrofuran, dimethylformamide, or alcohols (such as ethanol), preferably tetrahydrofuran or dimethylformamide. The aforesaid reaction is conducted at a temperature of about 20° C. to about 90° C., preferably about 50° C. to about 80° C., for a time period of about 5 minutes to about 8 hours.

A compound of formula IIIo can be prepared by reacting a compound of formula IVo, wherein L$^3$ is a leaving group, with a suitable base in a polar solvent. Suitable leaving groups include alkoxy (such as methoxy, ethoxy, or benzyloxy) or halo; preferably methoxy or ethoxy. Suitable bases include alkoxide bases, preferably sodium methoxide or sodium ethoxide. Suitable solvents include alcohols, preferably ethanol. The aforesaid reaction can be conducted at a temperature of about 0° C. to about 90° C., preferably of about 60° C. to about 90° C., for a period of about 1 hour to about 36 hours.

A compound of formula IVo can be prepared by reacting a compound of formula VI with the compound of formula Vo:

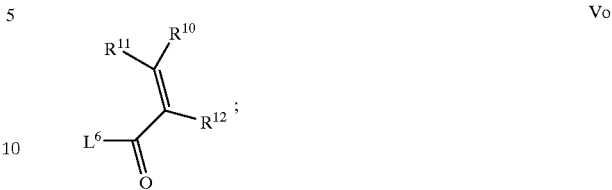

wherein L$^6$ is a suitable leaving group, in a suitable solvent. Suitable L$^6$ includes alkoxy or halo, such as chloro; preferably alkoxy; more preferably methoxy or ethoxy. Optionally, the aforesaid reaction may be conducted in the presence of a suitable tertiary amine base, such as triethylamine, N,N-dimethylaniline, or pyridine. Suitable solvents, include hydrocarbon solvents (benzene or toluene), tetrahydrofuran, or methylene chloride, preferably tetrahydrofuran. Preferably, the aforementioned reaction is conducted in tetrahydrofuran or dimethylformamide, in the presence of the aforementioned suitable tertiary amine base. The aforesaid reaction may be conducted at a temperature of about 20° C. to about 90° C., preferably about 50° C. to about 80° C., for a time period of about 30 minutes to about 6 hours.

In the aforesaid reactions, a compound of formula IVo may be isolated, but is preferably carried on to the next step without isolation. Thus, in Scheme 1, a compound of formula IIIo is preferably prepared in a one-pot preparation from a compound of the formula VI.

If the compounds of the formulae IVo are not isolated, the suitable solvent for the one-pot preparation is dimethylformamide, tetrahydrofuran, or alcohols, preferably alcohol, such as ethanol. The aforesaid one pot preparation is suitably conducted at a temperature of about 0° C. to about 70° C., preferably about 23° C. to about 60° C., for a time period of about 30 minutes to about 24 hours.

A compound of formula VI can prepared by reacting a compound of formula H$_2$N—X—Y-Z-G with a compound of the formula VII as described Scheme 1.

Scheme 3 refers to the preparation of compounds of the formula H$_2$N—X—Y-Z-G, which are intermediates useful in the preparation of compounds of formula I in Schemes 1 and 2. Referring to Scheme 3, compounds of formula H$_2$N—X—Y-Z-G can be prepared by reacting a compound of formula VIII with a reducing agent, such as tin II chloride, in the presence of a suitable acid, such as hydrochloric acid, in a polar protic solvent. Suitable solvents include an alcoholic solvent, water, or mixtures thereof, preferably a mixture of ethanol and water. The aforesaid reaction can be conducted at a temperature of about 40° C. to about 100° C. for a period of about 1 to about 12 hours.

Alternatively, the compounds of formula H$_2$N—X—Y-Z-G can be prepared by reacting a compound of formula VIII with hydrogen gas, at a pressure between atmospheric pressure and 50 psi, in the presence of a catalyst and a polar solvent. Suitable catalysts include a palladium or platinum catalyst, preferably Adams catalyst (i.e., platinum oxide), or palladium adsorbed on charcoal. Suitable solvents include an alcoholic solvent, preferably methanol. The aforesaid reaction can be conducted at a temperature of about 20° C. to about 50° C., preferably about 23° C., for a period of about 30 minutes to about 6 hours.

A compound of the formula VIII, wherein Y is oxygen, sulfur, —CH$_2$S—, —CH$_2$O—, >NR$^{14}$, —CH$_2$[N(R$^{14}$)]— or —SO$_2$[N(R$^{14}$)]—, can be prepared by reacting a compound of formula X, wherein the group $L^7$ is fluoro or chloro, with a compound of the formula:

G-Z-Y—H (IX)

wherein Y is oxygen, sulfur, —$CH_2S$—, —$CH_2O$—, >$NR^{14}$, —$CH_2[N(R^{14})]$— or —$SO_2[N(R^{14})]$—, in the presence of a base in a polar aprotic solvent. Suitable bases include an alkali metal hydride base; preferably sodium hydride. Suitable solvents include dimethylformamide, tetrahydrofuran or 1,2-dimethoxyethane; preferably dimethylformamide. The aforesaid reaction can be conducted at a temperature of about 40° C. to about 140° C., preferably about 80° C. to about 120° C., for about 1 hour to about 24 hours.

Alternatively, the aforesaid compound of formula VIII, wherein Y is oxygen, sulfur, —$CH_2S$—, —$CH_2O$—, >$NR^{14}$, —$CH_2[N(R^{14})]$— or —$SO_2[N(R^{14})]$—, can be prepared in presence of an alkali metal hydroxide base, preferably potassium hydroxide, optionally in the presence of a phase transfer catalyst, such as a quaternary ammonium or phosphonium salt, preferably tetrabutylammonium bromide, in an aromatic hydrocarbon solvent. Preferably the solvent is benzene or toluene. The aforesaid reaction can be conducted at a temperature of about 0° C. to about 120° C., preferably at about 23° C., for about 1 hour to about 12 hours.

Alternatively, the aforesaid compound of formula VIII, wherein Y is oxygen, sulfur, —$CH_2S$—, —$CH_2O$—, >$NR^{14}$, —$CH_2[N(R^{14})]$— or —$SO_2[N(R^{14})]$—, can be prepared under so called "Ulman coupling" conditions. Under such conditions, the aforesaid compound of formula VIII can be prepared by reacting a compound of formula X, wherein the group $L^7$ is bromo or chloro, with a compound of the formula:

G-Z-Y—H (IX)

wherein Y is oxygen, sulfur, —$CH_2S$—, —$CH_2O$—, >$NR^{14}$, —$CH_2[N(R^{14})]$— or —$SO_2[N(R^{14})]$—, in the presence of a base and a catalyst in a polar aprotic solvent. Suitable bases include an alkali metal carbonate or hydroxide base, preferably potassium carbonate. Suitable catalysts include a copper (0) catalyst, preferably finely powdered copper bronze. Suitable solvents include dimethylformamide or 1-methyl-2-pyrrolidinone. The aforesaid reaction can be conducted at a temperature of about 80° C. to about 140° C., for about 6 hours to about 24 hours.

A compound of formula VIII, wherein the group Y is in an oxidized state, i.e., >$SO_2$, >$S$=$O$, —$CH_2SO$—, —$CH_2SO_2$—, $SO(CH_2)_n$— or —$SO_2(CH_2)_n$—, can be prepared by reacting a corresponding compound of formula VIII, wherein the group Y is in a corresponding lower oxidation state, with a suitable oxidizing agent in a solvent. The corresponding lower oxidation state for each compound of formula VIII, wherein the group Y is >$SO_2$ and >$S$=$O$ is a compound of formula VIII, wherein the group Y is S. The corresponding lower oxidation state for each compound of formula VIII, wherein the group Y is —$CH_2SO_2$— and —$CH_2SO$— is a compound of formula VIII, wherein the group Y is —$CH_2S$—. The corresponding lower oxidation state for each compound of formula VIII, wherein the group Y is —$SO_2(CH_2)_n$— and —$SO(CH_2)_n$— is a compound of formula VIII, wherein the group Y is —$S$—$(CH_2)_n$— Suitable oxidizing agents include a peroxy acid, preferably peracetic acid, or an organic peroxide, preferably m-chloroperoxybenzoic acid or tert-butyl hydroperoxide. Suitable solvents include methylene chloride or alcohol, such as ethanol. The aforesaid reaction can be conducted at a temperature of about −10° C. to about 30° C., for about 1 hour to about 8 hours.

A compound of the formula VIII, wherein Y is —$O(CH_2)_n$—, —$S(CH_2)_n$— or —$NR^{14}(CH_2)_n$—, respectively, can be prepared by reacting a compound of the formula X, wherein the group $L^7$ is $L^8$—$(CH_2)_n$— and wherein the group $L^8$ is halo, such as chloro, bromo, iodo, mesyloxy (MsO), or tosyloxy (TsO), with a compound of formula:

G-Z-W—H (IX)

wherein the group W is oxygen, sulfur, or —$NR^{14}$, respectively, in the presence of a base in a polar aprotic solvent. Suitable bases include an alkali metal carbonate base, preferably potassium carbonate or cesium carbonate. Suitable solvents include dimethylformamide or tetrahydrofuran. The aforesaid reaction can be conducted at a temperature of about 23° C. to about 80° C., preferably about 20° C. to about 50° C., for about 1 to about 24 hours.

A compound of the formula VIII, wherein Y is >$C$=$O$, —$CH$=$CH$— or —$C$≡$C$—, can be prepared by reacting a compound of formula X, wherein the group $L^7$ is dihydroxyborane; zinc halide, such as zinc chloride; or trialkyl tin, such as tributyl tin, with a compound of the formula:

G-Z-Y-$L^9$ (IX)

wherein Y is >$C$=$O$, —$CH$=$CH$— or —$C$≡$C$—; and wherein the group $L^9$ is halo; preferably chloro, bromo or iodo; in the presence of a catalyst in a solvent. Suitable catalysts include a palladium or nickel catalyst, preferably tetrakis triphenyl phosphine palludium (0) $(Pd(PPh_3)_4)$. Suitable solvents include toluene, tetrahydrofuran, dimethylformamide, or dimethylsulfoxide. The aforesaid reaction can be conducted at a temperature of about 23° C. to about 110° C., for a period of about 1 hour to about 24 hours. Such reactions can be facilitated by the presence of a copper salt, such as cuprous iodide or cuprous bromide.

Alternatively, a compound of the formula VIII, wherein Y is —$C$≡$C$—, can be prepared by reacting a compound of formula X, wherein $L^7$ is halo or triflate, preferably bromo or iodo, with a compound of the formula:

G-Z-Y—H (IX)

in the presence of a base, such as a trialkylamine base, preferably triethylamine and a palladium catalyst, preferably $Pd(PPh_3)_4$ in a solvent. Suitable solvents include tetrahydrofuran or dimethylformamide. The aforesaid reaction can be conducted at a temperature of about 23° C. to about 60° C. for a period of about 1 to about 24 hours.

A compound of the formula VIII, wherein Y is —$CH_2(CH_2)_n$—, can be prepared by reacting the aforementioned compound of the formula VIII, wherein Y is —$CH$=$CH$— or —$C$≡$C$—, with hydrogen gas, at ambient pressure to about 50 psi, in the presence of a palladium catalyst in a solvent. Preferably the palladium catalyst is palladium adsorbed on charcoal. Suitable solvents include methanol or ethyl acetate. The aforesaid reaction can be conducted at a temperature of about 20° C. to about 50° C., for about 1 hour to about 24 hours.

Compounds of the formulae X and IX (i.e., compounds of the formulae G-Z-Y—H, G-Z-W—H, or G-Z-Y-$L^9$) are either commercially available or are well known and can be prepared by methods known to those skilled in the art.

The compounds of the formula I, which are basic in nature, are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations and then evaporating the resulting solution to dryness, preferably under reduced pressure.

Alternatively, these salts may also be prepared by mixing lower alkanolic solutions of the acidic compounds and the desired alkali metal alkoxide together and then evaporating the resulting solution to dryness in the same manner as before. In either case, stoichiometric quantities of reagents are preferably employed in order to ensure completeness of reaction and maximum product yields.

Biological Assays

The ability of the compounds of formula I or their pharmaceutically acceptable salts (hereinafter also referred to as the compounds of the present invention) to inhibit metalloproteinases or mammalian reprolysins and, consequently, demonstrate their effectiveness for treating diseases characterized by metalloproteinase activity is shown by the following in vitro and in vivo assay tests.

MMP Assays

MMP-13 selective inhibitors can be identified by screening the inhibitors of the present invention through the MMP fluorescence assays described below and selecting those agents with MMP-13/MMP-X inhibition $IC_{50}$ ratios of 100 or greater and potency of less than 100 nM, where MMP-X refers to one or more other MMP's.

Non-selective collagenase inhibitors as used herein, unless otherwise mentioned, refer to agents which exhibit less than a 100 fold selectivity for the inhibition of MMP-13 enzyme activity over MMP-X enzyme activity or a potency of more than 100 nM as defined by the $IC_{50}$ results from the MMP-13/MMP-X fluorescence assays described below.

The ability of collagenase inhibitors to inhibit collagenase activity is well known in the art. The degree of inhibition of a particular MMP for several compounds has been well documented in the art and those skilled in the art will know how to normalize different assay results to those assays reported herein. The following assays may be used to identify matrix metalloproteinase inhibitors.

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

$$10 \text{ mM} \rightarrow 120 \text{ μM} \rightarrow 12 \text{ μM} \rightarrow 1.2 \text{ μM} \rightarrow 0.12 \text{ μM}$$

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 μl is then added to appropriate wells of the microfluor plate. Final concentration of collagenase in the assay is 60 ng/ml.

Substrate (DNP-Pro-Cha-Gly-Cys(Me)-His-Ala-Lys (NMA)-$NH_2$) is made as a 5 mM stock in dimethylsulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 μM then the inhibitors are assayed at concentrations of 0.3 μM, 0.03 μM and 0.003 μM.

Inhibition of Gelatinase (MMP-2)

Human recombinant 72 kD gelatinase (MMP-2, gelatinase A) is activated for 16–18 hours with 1mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenylmercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM $CaCl_2$ and 0.05% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each-compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-$NH_2$ substrate (10 μM) under similar conditions as described above for the inhibition of human collagenase (MMP-1).

Human recombinant 92 kD gelatinase (MMP-9, gelatinase B) is activated for 2 hours with 1 mM p-aminophenylmercuric acetate (from a freshly prepared 100 mM stock in 0.2 N NaOH) at 37 C.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$, 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM and 0.03 µM.

Substrate (Dnp-Pro-Cha-Gly-Cys(Me)-His-Ala-Lys (NMA)-NH$_2$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

Collagen Film MMP-13 Assay

Rat type I collagen is radiolabeled with $^{14}C$ acetic anhydride (T. E. Cawston and A. J. Barrett, *Anal Boichem.*, 99, 340–345 (1979)) and used to prepare 96 well plates containing radiolabeled collagen films (Barbara Johnson-Wint, *Anal Boichem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM CaCl$_2$, 1 uM ZnCl$_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 µl of appropriate drug dilution and 100 µl of diluted enzyme are pipetted into wells of a 96 well plate containing collagen films labeled with $^{14}C$-collagen. The final enzyme concentration is 0.3 µg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were conducted using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were conducted as outlined above except that instead of using recombinant MMP-13 or recombinant MMP-1, cartilage conditioned medium was the enzyme source.

IL-1 Induced Cartilage Collagen Degradation from Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue is used because it: (1) is very similar to articular cartilage, (2) is readily available, (3) is relatively homogeneous and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1α (5 ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 µl) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 µg/ml trypsin is added to each well and incubation continued for a further 48 hours at 37° C. After 48 hours incubation in trypsin, the PBS solution is removed. Aliquots (50 µl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of TNF Production

The ability or inability of the compounds or the pharmaceutically acceptable salts thereof to inhibit the production of TNF is shown by the following in vitro assay:

Human Monocyte Assay

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 µl of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNF α using the R&D ELISA Kit.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 µCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 µM stock of each compound in DMEM in 96 well plate. Store in freezer overnight. The next day perform serial dilutions in DMEM with IL-1 to 5 µM, 500 nM and 50 nM. Aspirate final wash from wells and add 50 µl of compound from above dilutions to 450 µl of IL-1 media in appropriate wells of the 48 well plates. Final compound concentrations equal 500 nM, 50 nM and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 µl) followed by compound (50 µl) so as to initiate the assay. Plates are incubated at 37° C., with a 5% $CO_2$ atmosphere.

At 40–50 % release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 µl of papain digestion buffer (0.2 M Tris, pH 7.0, 5 mM EDTA, 5 mM DTT and 1 mg/ml papain) is added to each well. Plates with digestion solution are incubated at 60° C. overnight. The cell layer is removed from the plates the next day and placed in scintillation tubes. Scintillate is then added and samples counted (LSC).

The percent of released counts from the total present in each well is determined. Averages of the triplicates are made with control background subtracted from each well. The percent of compound inhibition is based on IL-1 samples as 0% inhibition (100% of total counts).

The compounds of the present invention that were tested all have $IC_{50}$'s in at least one of the above assays of less than 100 µM preferably less than 100 nM. Certain preferred groups of compounds possess differential selectivity toward the various MMP's or ADAMs. One group of preferred compounds possesses selective activity towards MMP-13 over MMP-1. Another preferred group of compounds possesses selective activity towards MMP-13 over MMP-1, MMP-3 and MMP-7. Another preferred group of compounds possesses selective activity towards MMP-13 over MMP-1, MMP-3, MMP-7 and MMP-17. Another preferred group of compounds possesses selective activity towards MMP-13 over MMP-1, MMP-2, MMP-3, MMP-7, MMP-9 and MMP-14 Another preferred group of compounds possesses selective activity towards MMP-13 over MMP-12 and MMP-14.

For administration to mammals, including humans, for the inhibition of matrix metalloproteinases, a variety of conventional routes may be used including oral, parenteral (e.g., intravenous, intramuscular or subcutaneous), buccal, anal and topical. In general, the compounds of the invention (hereinafter also known as the active compounds) will be administered at dosages of about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials can also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers can be added to increase viscosity or for sustained release (such as cellulosic polymers, Dextran, polyethylene glycol, or alginic acid). These solutions are suitable for intraorbital injection purposes. The preparation of all these solutions under sterile conditions is readily accomplished by standard pharmaceutical techniques well known to those skilled in the art. In the case of animals, compounds can be administered intraorbitally at dosage levels of about 0.1 to 50 mg/kg/day, advantageously 0.2 to 10 mg/kg/day given in a single dose or up to 3 divided doses.

As with the other routes of administration and corresponding dosage forms described herein, dosage forms intended for oral administration are also suitably formulated to provide controlled-, sustained- and/or delayed release of the active ingredient. Typically, these would include delayed-release oral tablets, capsules and multiparticulates, as well as enteric-coated tablets and capsules which prevent release and adsorption of the active ingredient in the stomach of the patient and facilitate enteric delivery distal to the stomach, i.e., in the intestine. Other typical oral dosage forms would include sustained-release oral tablets, capsules and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure or in vacuo means that a rotary evaporator was used.

General Experimentals

General Example:

Compounds of the formula I can be prepared by reacting the appropriate compound of formula III with a urea of the formula II (i.e., H$_2$N(CO)—NH$_2$) in the presence of a suitable base, such as an alkoxide base, preferably sodium ethoxide, in a polar solvent, such as an alcoholic solvent, preferably ethanol, at a temperature of 20° C. to the boiling point of the solvent, preferably 80° C. for 15 minutes to 3 hours.

General Preparation:

A compound of formula III can be prepared by reacting an appropriate compound of formula IV with a suitable base, such as a tertiary amine base or a polymer bound base, preferably Amberlyst-400® resin (hydroxide form), in a polar solvent, such as an alcoholic solvent, preferably ethanol, at a temperature of about 0° C. to about 50° C., preferably about 20° C., for a period of about 6 to about 36 hours.

The compound of formula IV can be prepared by reacting the appropriate compound of the formula VI with a compound of the formula V, which has a general formula of L$^3$-(A')-L$^4$ or L$^3$-(A'), in an aprotic solvent, preferably and aromatic hydrocarbon solvent such as benzene or toluene, at a temperature of about 40° C. and the boiling point of the solvent, preferably about 80° C., for a period of about 1 to about 6 hours.

The compound of formula VI can be prepared by reacting the appropriate compound of the formula NH$_2$—X—Y-Z-G with a compound of the formula VII, which is a 2-halo malonate ester, preferably 2-bromodiethyl malonate, in the presence of a suitable base, such as a tertiary amine base, preferably N,N-dimethylaniline, at a temperature of about 20° C. to about 100° C., preferably about 80° C., for a period of about 4 to about 48 hours.

EXAMPLE 1

| 1-[6-(4-BROMO-PHENOXY)-PYRIDIN-3-YL]-1,7,9-TRIAZA-SPIRO[4.5]DECANE-2,6,8,10-TETRAONE: | | | |
|---|---|---|---|
| Example Number | Structure | Molecular Weight | MS (APCl, m/z): [M + H]$^+$ |
| 1 | [structure] | 445.238 | 445 |

Sodium metal (29 mg, 1.26 mmol) was added to 1.3 mL of ethanol and stirred until homogeneous. of 1-[6-(4-Bromo-phenoxy)-pyridin-3-yl]-pyrrolidine-2,2-dicarboxylic acid diethyl ester (0.20 g, 0.42 mmol) was added, followed by urea (75 mg, 1.26 mmol) and the mixture was stirred for 5 minutes at 80° C. The mixture was cooled to ambient temperature, acidified with 1M hydrochloric acid and extracted 3× with ethyl acetate. The combined organic phases were dried over sodium sulphate, filtered and concentrated in vacuo. The residue was purified by silica gel chromatography (3:1 hexane-ethyl acetate), affording 28 mg of 1-[6-(4-Bromo-phenoxy)-pyridin-3-yl]-1,7,9-triaza-spiro [4.5]decane-2,6,8,10-tetraone as a colorless solid. HPLC Ret. time: 2.201 min; MS (APCl, m/z): 436 [M−H]$^-$; 438 [M+H]$^+$.

Preparation 1:

2-(4-Bromo-phenoxy)-5-nitro-pyridine:

4-Bromophenol (5.5 g, 32 mmol) was added to 42 mL of 50% w/w aqueous sodium hydroxide. After stirring for 30 min, 44 mL of toluene was added, followed by 2-chloro-5-nitropyridine (5.0 g, 32 mmol) and tetrabutylammonium bromide (10 g, 32 mmol). After stirring for 1.5 hours at 23° C., the mixture was diluted with 200 mL of water, neutralized with 12M aqueous hydrochloric acid and the mixture was extracted 3× with ether. The combined organic layers were dried over MgSO$_4$, filtered and concentrated in vacuo, affording 6 g of 2-(4-bromo-phenoxy)-5-nitro-pyridine. 1H NMR (CDCl$_3$, 500 MHz): 9.05 (d, 1H, J=3.5 Hz), 8.51 (dd, 1H, J=3.5, 9.5 Hz), 7.58 (d, 2H, J=9.0 Hz), 7.08 (m, 3H) ppm. MS (APCl, m/z): 295 [M+H]$^+$.

6-(4-Bromo-phenoxy)-pyridin-3-ylamine:

A mixture of 2-(4-bromo-phenoxy)-5-nitro-pyridine (6.0 g, 22.7 mmol), 200 mL of methanol and 50 mg of PtO$_2$ was shaken under 50 psi of H$_2$ for 1 hour at 23° C. The mixture was filtered through a pad of celite® and the filtrate was concentrated in vacuo, affording 6 g of 6-(4-bromo-phenoxy)-pyridin-3-ylamine. 1H NMR (CD$_3$OD, 500 MHz): 7.65 (d, 1H, J=3.5 Hz), 7.48 (d, 2H, J=8.5 Hz), 7.25 (dd, 1H, J=3.5, 9.0 Hz), 6.91 (d, 2H, J=9.0 Hz), 6.80 (d, 1H, J=9.0 Hz) ppm. MS (APCl, m/z): 265 [M+H]$^+$.

Preparation 2:

1-[6-(4-Bromo-phenoxy)-pyridin-3-yl]-pyrrolidine-2,2-dicarboxylic acid diethyl ester:

A mixture of of 6-(4-bromo-phenoxy)-pyridin-3-ylamine (4.5 g, 16.9 mmol), 2-bromodimethylmalonate (4.1 g, 17 mmol) and N,N-dimethylaniline (2.1 g, 17 mmol) was stirred at 80° C. for 24 hours. The mixture was cooled to 23° C., diluted with 50 mL of benzene and was treated with 7 mL of 2-bromopropionyl chloride. After stirring at reflux for 3 h, the mixture was cooled to 23° C., concentrated in vacuo and was diluted with 750 mL of ethanol. Amberlyst-400 (hydroxide form) resin (75 g) was added and the mixture was stirred for 24 hours at 23° C. The mixture was filtered and the resin was washed with 50 mL of methanol. The filtrate was concentrated in vacuo and the residue was purified by silica gel chromatography (2:1 hexane-ethyl acetate), affording 6 g of 1-[6-(4-bromo-phenoxy)-pyridin-3-yl]-pyrrolidine-2,2-dicarboxylic acid diethyl ester. 1H NMR (CDCl$_3$, 500 MHz): 8.06 (d, 1H, J=2.5 Hz), 7.75 (dd, 1H, J=2.5, 8.0 Hz), 7.52 (d, 2H, J=9.0 Hz), 7.04 (d, 2H, J=8.5 Hz), 6.95 (d, 1H, J=9.0 Hz), 4.22 (q, 4H, J=7.0 Hz), 2.75 (m, 2H), 2.66 (m, 2H), 1.12 (t, 6H, J=7.5 Hz) ppm. MS (APCl, m/z): 479 [M+H]$^+$.

The following compounds were prepared according to methods analogous to that of Example 1, substituting where appropriate the correct pyridine and diester:

TABLE 1

| Example Number | Structure | Molecular Weight | MS (APCl, m/z): [M + H]+ |
|---|---|---|---|
| 2 | (structure) | 384.327 | 385.1 |
| 3 | (structure) | 398.354 | 399.1 |

EXAMPLE 4

4-[5-(2,6,8,10-TETRAOXO-1,7,9-TRIAZA-SPIRO[4.5]DEC-1-YL)-PYRIDIN-2-YLOXY]-BENZONITRILE:

| Example Number | Structure | Molecular Weight | MS (APCl, m/z): [M + H]+ |
|---|---|---|---|
| 4 | (structure) | 391.346 | 392.1 |

Following the procedure for pyrimidinetrione formation outlined in Example 1, reaction of 1-[6-(4-Cyano-phenoxy)-pyridin-3-yl]-pyrrolidine-2,2-dicarboxylic acid diethyl ester (58 mg, 0.14 mmol) with urea (0.030 g, 0.5 mmol) in 0.5 mL of 1M sodium ethoxide in ethanol afforded 14.3 mg of 4-[5-(2,6,8,10-Tetraoxo-1,7,9-triaza-spiro[4.5]dec-1-yl)-pyridin-2-yloxy]-benzontrile as a colorless solid. 1H NMR (CD$_3$OD, 500 MHz): 8.06 (d, 1H, J=3.5 Hz), 7.78 (m, 3H), 7.31 (d, 2H, J=8.5 Hz), 7.13 (d, 1H, J=9.0 Hz), 2.75 (m, 2H), 2.68 (m, 2H) ppm. MS (APCl, m/z): 390 [M−H]−; 392 [M+H]+.

Preparation 1:
1-[6-(4-Cyano-phenoxy)-pyridin-3-yl]-pyrrolidine-2,2-dicarboxylic acid diethyl ester:

A mixture of 1-[6-(4-bromo-phenoxy)-pyridin-3-yl]-pyrrolidine-2,2-dicarboxylic acid diethyl ester (0.28 g, 0.53 mmol), zinc cyanide (0.037 g, 0.32 mmol), tetrakistriphenylphosphine palladium (0) (0.024 g, 0.021 mmol) and 0.66 mL of dimethylformamide was heated to 80° C. for 24 hours. An additional 37 mg of zinc cyanide and 24 mg of tetrakistriphenylphosphine palladium (0) was added and the mixture was stirred at 80° C. for an additional 48 hours. After cooling to room temperature, the mixture was diluted with toluene and was washed with 2M ammonium hydroxide (twice), brine, dried over sodium sulphate, filtered and concentrated in vacuo. Purification by radial chromatography (ethyl acetate-hexanes, then methanol) afforded 58 mg of 1-[6-(4-Cyano-phenoxy)-pyridin-3-yl]-pyrrolidine-2,2- dicarboxylic acid diethyl ester as a colorless syrup. 1H NMR (CDCl$_3$, 500 MHz): 8.07 (d, 1H, J=3.5 Hz), 7.80 (dd, 1H, J=2.5, 9.0 Hz), 7.69 (d, 2H, J=9.0 Hz), 7.25 (d, 2H, J=9.0 Hz), 7.02 (d, 1H, J=9.0 Hz), 4.21 (q, 4H, J=7.5 Hz), 2.74 (m, 2H), 2.66 (m, 2H), 1.19 (t, 6H, J=7.0 Hz) ppm. MS (APCl, m/z): 424 [M+H]$^+$.

| 1-[6-(4-[1,3,4]OXADIAZOL-2-YL-PHENOXY)-PYRIDIN-3-YL]-1,7,9-TRIAZA-SPIRO[4.5]DECANE-2,6,8,10-TETRAONE: | | | |
|---|---|---|---|
| Example Number | Structure | Molecular Weight | MS (APCl, m/z): [M + H]$^+$ |
| 5 | | 434.371 | 435.1 |

Following the procedure for pyrimidinetrione formation outlined in Example 1, reaction of 1-[6-(4-[1,3,4]oxadiazol-2-yl-phenoxy)-pyridin-3-yl]-5-oxo-pyrrolidine-2,2-dicarboxylic acid diethyl ester (200 mg, 0.44 mmol) with urea (0.080 g, 1.3 mmol) in 1.3 mL of 1M sodium ethoxide in ethanol afforded 25 mg of 1-[6-(4-[1,3,4]oxadiazol-2-yl-phenoxy)-pyridin-3-yl]-1,7,9-triaza-spiro[4,5]decane-2,6,8,10-tetraone as a colorless solid. 1H NMR (CD$_3$OD, 500 MHz): 9.02 (s, 1H), 8.14 (d, 2H, J=8.0 Hz), 8.06 (d, 1H, J=2.0 Hz), 7.78 (dd, 1H, J=2.5, 9.0 Hz), 7.35 (d, 2H, J=9.0 Hz), 7.12 (d, 1H, J=9.0 Hz), 2.74 (m, 2H), 2.66 (m, 2H) ppm. MS (APCl, m/z): 435 [M+H]$^+$.

Preparation 1:

1-[6-(4-Carboxy-phenoxy)-pyridin-3-yl]-5-oxo-pyrrolidine-2,2-dicarboxylic acid diethyl ester:

A mixture of 1-[6-(4-Formyl-phenoxy)-pyridin-3-yl]-pyrrolidine-2,2-dicarboxylic acid diethyl ester (0.70 g, 1.64 mmol), sodium carbonate (0.26 g, 1.64 mmol) and 16.4 mL of 1:1 tert-butyl alcohol-water was treated with potassium permanganate (0.26 g, 1.64 mmol). After stirring for 2 hours at room temperature, the mixture was quenched with sodium sulfite, acidified with 1M hydrochloric acid and extracted 3× with ethyl acetate. The combined organic layers were dried over sodium sulphate, filtered and concentrated in vacuo, affording 1-[6-(4-Carboxy-phenoxy)-pyridin-3-yl]-5-oxo-pyrrolidine-2,2-dicarboxylic acid diethyl ester as a colorless syrup (0.5 g). 1H NMR (CDCl$_3$, 500 MHz): 8.14 (d, 2H, J=8.5 Hz), 8.10 (d, 1H, J=3.0 Hz), 7.80 (dd, 1H, J=2.5, 8.5 Hz), 7.24 (d, 2H, J=8.0 Hz), 7.02 (d, 1H, J=9.0 Hz), 4.21 (q, 4H, J=7.0 Hz), 2.74 (m, 2H), 2.66 (m, 2H), 1.21 (t, 6H, J=7.5 Hz) ppm. MS (APCl, m/z): 443 [M+H]$^+$.

Preparation 2:

1-[6-(4-Hydrazinocarbonyl-phenoxy)-pyridin-3-yl]-5-oxo-pyrrolidine-2,2-dicarboxylic acid diethyl ester:

A mixture of affording 1-[6-(4-Carboxy-phenoxy)-pyridin-3-yl]-5-oxo-pyrrolidine-2,2-dicarboxylic acid diethyl ester (0.4 g, 0.97 mmol), 1-hydroxybenzotriazole hydrate (0.176 g, 1.3 mmol), 1,2-dichloroethane (0.25 g, 1.3 mmol) and 6 mL of methylene chloride was stirred at room temperature for 20 minutes. The mixture was treated with boc-hydrazide (0.17 g, 1.3 mmol) and stirred at room temperature overnight. The mixture was diluted with ethyl acetate, washed with 1M hydrochloric acid, sodium bicarbonate solution, brine, dried over sodium sulphate, filtered and concentrated in vacuo. The residue was dissolved in 5 mL of 1:1 V/V methylene chloride-trifluoroacetic acid, stirred for 1 hours at ambient temperature and was concentrated in vacuo. The residue was dissolved in ethyl acetate, washed with 1M sodium hydroxide, brine, dried over sodium sulphate, filtered and concentrated, affording 1-[6-(4-Hydrazinocarbonyl-phenoxy)-pyridin-3-yl]-5-oxo-pyrrolidine-2,2-dicarboxylic acid diethyl ester (0.20 g) as a colorless syrup. HPLC: 2.770 min.

Preparation 3:

1-[6-(4-[1,3,4]oxadiazol-2-yl-phenoxy)-pyridin-3-yl]-5-oxo-pyrrolidine-2,2-dicarboxylic acid diethyl ester:

A mixture of affording 1-[6-(4-Hydrazinocarbonyl-phenoxy)-pyridin-3-yl]-5-oxo-pyrrolidine-2,2-dicarboxylic acid diethyl ester (0.20 g, 0.44 mmol), trimethylorthoformate (0.1 mL, 0.91 mmol) and 1 mL of xylenes was refluxed for 24 hours. The mixture was concentrated in vacuo, affording 1-[6-(4-[1,3,4]oxadiazol-2-yl-phenoxy)-pyridin-3-yl]-5-oxo-pyrrolidine-2,2-dicarboxylic acid diethyl ester (0.2 g) as a colorless syrup. MS (APCl, m/z): 467.2 [M+H]$^+$.

EXAMPLE 6

| 1-[6-(4-ETHYL-PHENOXY)-PYRIDIN-3-YL]-1,7,9-TRIAZA-SPIRO[4.5]DECANE-2,6,8,10-TETRAONE: | | | |
|---|---|---|---|
| Example Number | Structure | Molecular Weight | MS (APCl, m/z): [M + H]$^+$ |
| 6 | | 394.39 | 395.3 |

Following the procedure for pyrimidinetrione formation outlined in Example 1, reaction of 1-[6-(4-ethyl-phenoxy)-pyridin-3-yl]-5-oxo-pyrrolidine-2,2-dicarboxylic acid diethyl ester (200 mg, 0.41 mmol) with urea (0.088 g, 1.4 mmol) in 1.4 mL of 1M sodium ethoxide in ethanol afforded 25 mg of 1-[6-(4-[1,3,4]oxadiazol-2-yl-phenoxy)-pyridin-3-yl]-1,7,9-triaza-spiro[4.5]decane-2,6,8,10-tetraone as a colorless solid. 1H NMR (CDCl$_3$, 500 MHz): 8.73 (bs, 2H), 7.97 (d, 1H, J=2.0 Hz), 7.78 (d, 1H, J=8.5 Hz), 7.22 (d, 2H, J=8.5 Hz), 7.05 (d, 2H, J=9.0 Hz), 6.91 (d, 1H, J=9.0 Hz), 2.81 (q, 2H, J=7.5 Hz), 2.74 (m, 2H), 2.64 (m, 2H), 1.26 (t, 3H, J=8.0 Hz) ppm.

Preparation 1:

1-[6-(4-Ethyl-phenoxy)-pyridin-3-yl]-5-oxo-pyrrolidine-2,2-dicarboxylic acid diethyl ester:

A mixture of 1-[6-(4-vinyl-phenoxy)-pyridin-3-yl]-pyrrolidine-2,2-dicarboxylic acid diethyl ester (0.20 g), 50 mg of 10% palladium on charcoal and 20 mL of ethyl acetate was shaken under 50 psi of hydrogen gas for 2 hours. The mixture was filtered and concentrated in vacuo, affording 0.20 g of 1-[6-(4-ethyl-phenoxy)-pyridin-3-yl]-5-oxo-pyrrolidine-2,2-dicarboxylic acid diethyl ester as a colorless syrup. 1H NMR (CDCl$_3$, 500 MHz): 8.08 (d, 1H, J=2.5 Hz), 7.73 (dd, 1H, J=2.5, 8.5 Hz), 7.24 (d, 2H, J=7.5 Hz), 7.05 (d, 2H, J=8.0 Hz), 6.89 (d, 1H, J=9.0 Hz), 4.21 (q, 4H, J=7.0 Hz), 2.74 (m, 2H), 2.65 (m, 4H), 1.27 (t, 3H, J=8.0 Hz), 1.20 (t, 6H, J=7.5 Hz) ppm.

EXAMPLE 7

| Example Number | Structure | Molecular Weight | MS (APCl, m/z): [M + H]$^+$ |
|---|---|---|---|
| | N-{4-[5-(2,6,8,10-TETRAOXO-1,7,9-TRIAZA-SPIRO[4.5]DEC-1-YL)-PYRIDIN-2-YLOXY]-BENZYL}-ACETAMIDE: | | |
| 7 | 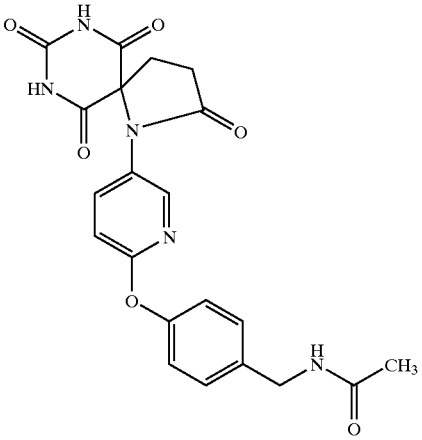 | 437.415 | 438.2 |

A mixture of 1-{6-[4-(tert-butoxycarbonylamino-methyl)-phenoxy]-pyridin-3-yl}-pyrrolidine-2,2-dicarboxylic acid diethyl ester (0.52 mmol) and 2 mL of a 1:1 v/v solution of trifluoroacetic acid in methylene chloride was stirred for 1 hours at ambient temperature and was then concentrated in vacuo. The residue was dissolved in 2.6 mL of methylene chloride and was treated with MMP-resin (polymer bound N-methyl morpholine-type base, 0.86 g, 1.75 mmol) and was treated with acetyl chloride (0.055 g, 0.7 mmol). After shaking for 24 h, the mixture was filtered and the resin was washed with methylene chloride. The combined filtrates were concentrated in vacuo, dissolved in 1.5 mL of 1M sodium ethoxide in ethanol and treated with 94 mg of urea. After stirring for 10 minutes at 80° C., the mixtures were treated with 2 g of a polystyrene-bound sulfonic acid resin, filtered and the resin was washed with 10 mL of 2M ammonia in methanol. The combined filtrates were concentrated in vacuo and purified by reverse-phase chromatography (acetonitrile-water-trifluoroacetic acid eluent) followed by radial chromatography (10% methanol-methylene chloride), affording: N-{4-[5-(2,6,8,10-Tetraoxo-1,7,9-triaza-spiro[4.5]dec-1-yl)-pyridin-2-yloxy]-benzyl}-acetamide as a colorless solid. HPLC Ret. time: 2.201 min; MS (APCl, m/z): 436 [M−H]$^-$; 438 [M+H]$^+$.

Preparation 1:

1-[6-(4-vinyl-phenoxy)-pyridin-3-yl]-pyrrolidine-2,2-dicarboxylic acid diethyl ester:

A mixture of 1-[6-(4-bromo-phenoxy)-pyridin-3-yl]-pyrrolidine-2,2-dicarboxylic acid diethyl ester (5.8 g, 12.2 mmol), vinyltributyltin (3.9 mL, 12.3 mmol), tetrakistriphenylphosphine palladium (0) (0.60 g, 0.52 mmol) and 24 mL of toluene was heated to reflux for 1 hour. After cooling to room temperature, the mixture was concentrated in vacuo and purified by silica gel chromatography (Flash 40, 20%–50% ethyl acetate-hexanes), affording 4.8 g of 1-[6-(4-Vinyl-phenoxy)-pyridin-3-yl]-pyrrolidine-2,2-dicarboxylic acid diethyl ester as a colorless syrup.

Preparation 2:

1-[6-(4-Formyl-phenoxy)-pyridin-3-yl]-pyrrolidine-2,2-dicarboxylic acid diethyl ester:

A mixture of 1-[6-(4-Vinyl-phenoxy)-pyridin-3-yl]-pyrrolidine-2,2-dicarboxylic acid diethyl ester (4.8 g, 11.3 mmol), sodium metaperiodate (4.8 g, 22 mmol), osmium tetroxide (10 mg) and 2:1 dioxane-water (189 mL) was stirred for 6 hours at ambient temperature. The mixture was quenched with sodium sulfite, diluted with water and extracted 3× with ethyl acetate. The combined organic phases were dried over sodium sulphate, filtered and concentrated in vacuo affording 1-[6-(4-Formyl-phenoxy)-pyridin-3-yl]-pyrrolidine-2,2-dicarboxylic acid diethyl ester as a colorless syrup (4.6 g).

Preparation 3:

1-{6-[4-(tert-Butoxycarbonylamino-methyl)-phenoxy]-pyridin-3-yl}-pyrrolidine-2,2-dicarboxylic acid diethyl ester:

A mixture of 1-[6-(4-Formyl-phenoxy)-pyridin-3-yl]-pyrrolidine-2,2-dicarboxylic acid diethyl ester (0.1 g, 0.24 mmol), tert-butoxycarbonylamide (0.083 g, 0.71 mmol), triethylsilane (0.11 mL, 0.083 g, 0.71 mmol) and acetonitrile (1 mL) was treated with trifluoroacetic acid (0.035 mL, 0.46 mmol) and stirred for 48 at ambient temperature. The mixture was diluted with ethyl acetate, washed with saturated sodium bicarbonate solution, brine, dried over sodium sulphate, filtered and concentrated in vacuo, affording 1-{6-[4-(tert-Butoxycarbonylamino-methyl)-phenoxy]-pyridin- 3-yl}-pyrrolidine-2,2-dicarboxylic acid diethyl ester as a colorless syrup.

The following compounds were prepared according to methods analogous to that of Example 7, submitting where appropriate the correct pyridine and diester:

TABLE 2

| Example Number | Structure | Molecular Weight | MS (APCl, m/z): [M + H]+ |
|---|---|---|---|
| 8 | 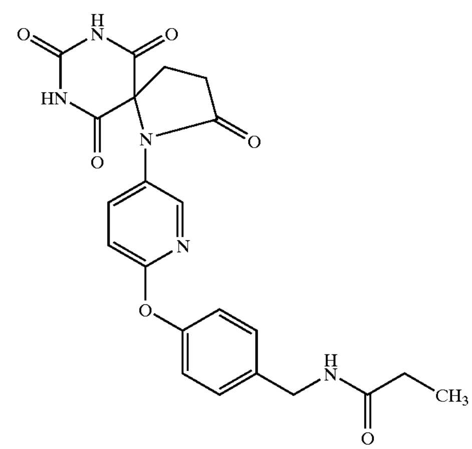 | 451.443 | 452.2 |
| 9 | 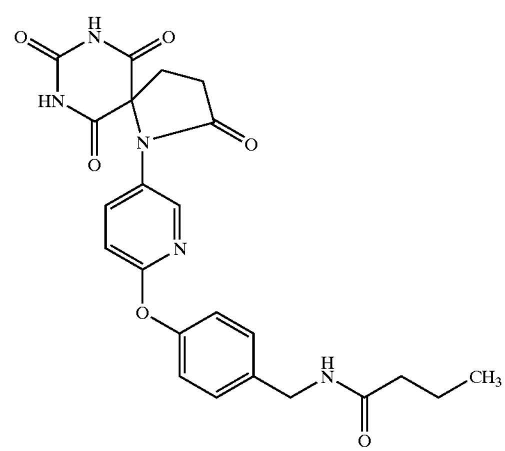 | 465.47 | 466.2 |
| 10 | 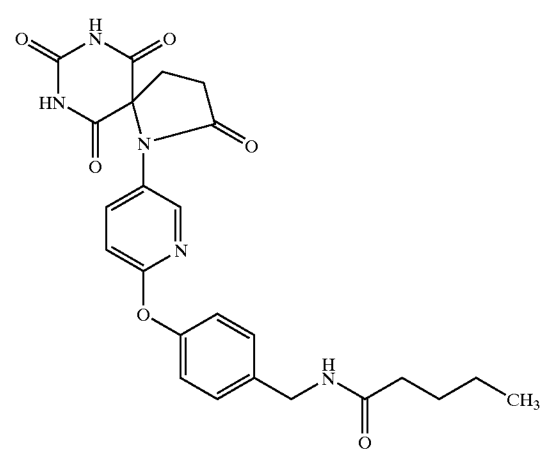 | 479.497 | 480.2 |

TABLE 2-continued

| Example Number | Structure | Molecular Weight | MS (APCl, m/z): [M + H]⁺ |
|---|---|---|---|
| 11 | 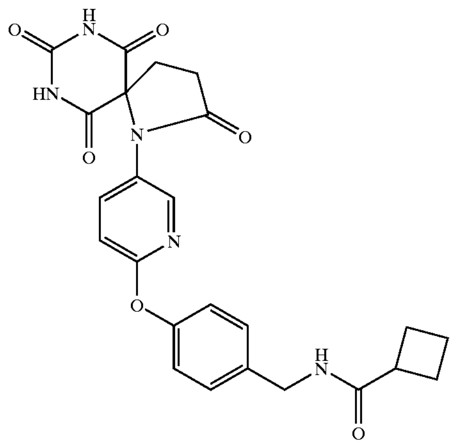 | 477.481 | 478.4 |

EXAMPLE 12

| 1-[6-(4-PYRAZOL-1-YLMETHYL-PHENOXY)-PYRIDIN-3-YL]-1,7,9-TRIAZA-SPIRO[4.5]DECANE-2,6,8,10-TETRAONE: | | | |
|---|---|---|---|
| Example Number | Structure | Molecular Weight | MS (APCl, m/z): [M + H]⁺ |
| 12 | | 446.43 | 447.2 |

Following the procedure for pyrimidinetrione formation outlined in Example 1, reaction of 5-oxo-1-[6-(4-pyrazol-1-ylmethyl-phenoxy)-pyridin-3-yl]-pyrrolidine-2,2-dicarboxylic acid diethyl ester (0.2 g, 0.4 mmol) with urea (0.074 g, 1.2 mmol) in 1.2 mL of 1M sodium ethoxide in ethanol afforded 6 mg of 1-[6-(4-Pyrazol-1-ylmethyl-phenoxy)-pyridin-3-yl]-1,7,9-triaza-spiro[4.5]decane-2,6,8,10-tetraone as a colorless solid. $^1$H NMR (CD$_3$OD, 500 MHz): 7.99 (d, 1H, J=2.5 Hz), 7.72 (m, 2H), 7.53 (d, 1H, J=2.5 Hz), 7.29 (d, 2H, J=8.5 Hz 7.10 (d, 2H, J=8.5 Hz), 6.97 (d, 1H, J=8.5 Hz), 6.35 (t, 1H, J=2.0 Hz), 5.38 (s, 2H), 2.75 (m, 2H), 2.65 (m, 2H) ppm. MS (APCl, m/z): 447.2 [M+H]⁺.

Preparation 1:

1-[6-(4-Hydroxymethyl-phenoxy)-pyridin-3-yl]-5-oxo-pyrrolidine-2,2-dicarboxylic acid diethyl ester:

1-[6-(4-Hydroxymethyl-phenoxy)-pyridin-3-yl]-5-oxo-pyrrolidine-2,2-dicarboxylic acid diethyl ester: To a solution of 1-[6-(4-formyl-phenoxy)-pyridin-3-yl]-pyrolidine-2,2-dicarboxylic acid diethyl ester (1.0 g, 2.3 mmol) in 30 mL of ethanol was added sodium borohydride (0.090 g, 2.3 mmol) at 0° C. After stirring for 3 hours, the mixture was concentrated in vacuo, diluted with ethyl acetate and water, and the aqueous layer was cautiously acidified with 1M hydrochloric acid, then neutralized with saturated aqueous sodium bicarbonate. The mixture was extracted three times with ethyl acetate, and the combined organic layers were dried over sodium sulfate, filtered and concentrated in vacuo, affording 0.80 g (80%) of 1-[6-(4-hydroxymethyl-phenoxy)-pyridin-3-yl]-5-oxo-pyrrolidine-2,2-dicarboxylic acid diethyl ester as a colorless syrup. $^1$H NMR (CDCl$_3$, 400 MHz): 8.04 (d, 1H, J=2.4 Hz), 7.72 (dd, 1H, J=2.4, 8.8 Hz), 7.40 (d, 2H, J=8.8 Hz), 7.12 (d, 2H, J=8.4 Hz), 6.91 (d, 1H, J=8.8 Hz), 4.70 (s, 2H), 4.19 (q, 4H, J=7.6 Hz), 2.75 (m, 2H), 2.65 (m, 2H), 1.18 (t, 6H, J=7.2 Hz) ppm. MS (APCl, m/z): 429.1 [M+H]⁺.

Preparation 2:

1-[6-(4-Bromomethyl-phenoxy)-pyridin-3-yl]-5-oxo-pyrrolidine-2,2-dicarboxylic acid diethyl ester:

To a solution of 1-[6-(4-hydroxymethyl-phenoxy)-pyridin-3-yl]-5-oxo-pyrrolidine-2,2-dicarboxylic acid diethyl ester (0.80 g, 1.9 mmol) in 9.4 mL of methylene chloride was added triethylamine (0.46 mL, 0.33 g, 3.3 mL). After cooling to −40° C., the mixture was treated with methanesulfonyl chloride (0.20 mL, 0.30 g, 2.61 mmol). After stirring for 1 hour, an additional 0.10 mL of methanesulfonyl chloride and 0.4 mL of triethylamine were added, and stirring was continued for 1 hour. A solution of anhydrous lithium bromide (1.6 g, 19 mmol, flame dried under vacuum before use) in tetrahydrofuran (20 mL) was added via cannula, and the mixture was warmed to room temperature and stirred for 2 hours. The mixture was diluted with ethyl acetate, and the organic phase was washed with water, dried over sodium sulfate, filtered and concentrated in vacuo. The residue was filtered through a pad of silica gel eluting with 1:1 ethyl acetate-hexanes, affording 0.65 g of 1-[6-(4-bromomethyl-phenoxy)-pyridin-3-yl]-5-oxo-pyrrolidine-2,2-dicarboxylic acid diethyl ester as a colorless syrup. $^1$H NMR (CDCl$_3$, 500 MHz): 8.07 (d, 1H, J=3.0 Hz), 7.76 (dd, 1H, J=2.5, 8.5 Hz), 7.44 (d, 2H, J=8.5 Hz), 7.12 (d, 2H, J=8.0 Hz), 6.95 (d, 1H, J=9.0 Hz), 4.53 (s, 2H), 4.22 (q, 4H, J=7.0 Hz), 2.75 (m, 2H), 1.20 (t, 6H, J=7.0 Hz) ppm.

Preparation 3:

5-Oxo-1-[6-(4-pyrazol-1-ylmethyl-phenoxy)-pyridin-3-yl]-pyrrolidine-2,2-dicarboxylic acid diethyl ester:

To a solution of 1-[6-(4-bromomethyl-phenoxy)-pyridin-3-yl]-5-oxo-pyrrolidine-2,2-dicarboxylic acid diethyl ester (0.2 g, 0.4 mmol) in 0.8 mL of dimethylformamide was added pyrazole (0.056 g, 0.82 mmol) and potassium carbonate (0.11 g, 0.82 mmol). After stirring for 24 hours at 50° C., the mixture was diluted with water, extracted three times with ethyl acetate, and the combined organic phases were dried over sodium sulfate, filtered and concentrated in vacuo, affording the crude product as a colorless syrup that was used directly in the next step. MS (APCl, m/z): 479.2 [M+H]$^+$.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed and such expected variations or differences in the results are contemplated in accordance with the objects and practices of the present invention. It is intended, therefore, that the invention be defined by the scope of the claims which follow and that such claims be interpreted as broadly as is reasonable.

We claim:

1. A compound of the formula:

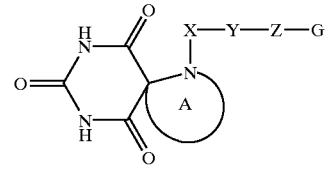

wherein said "A" is a 5 membered heterocyclic ring selected from the group consisting of:

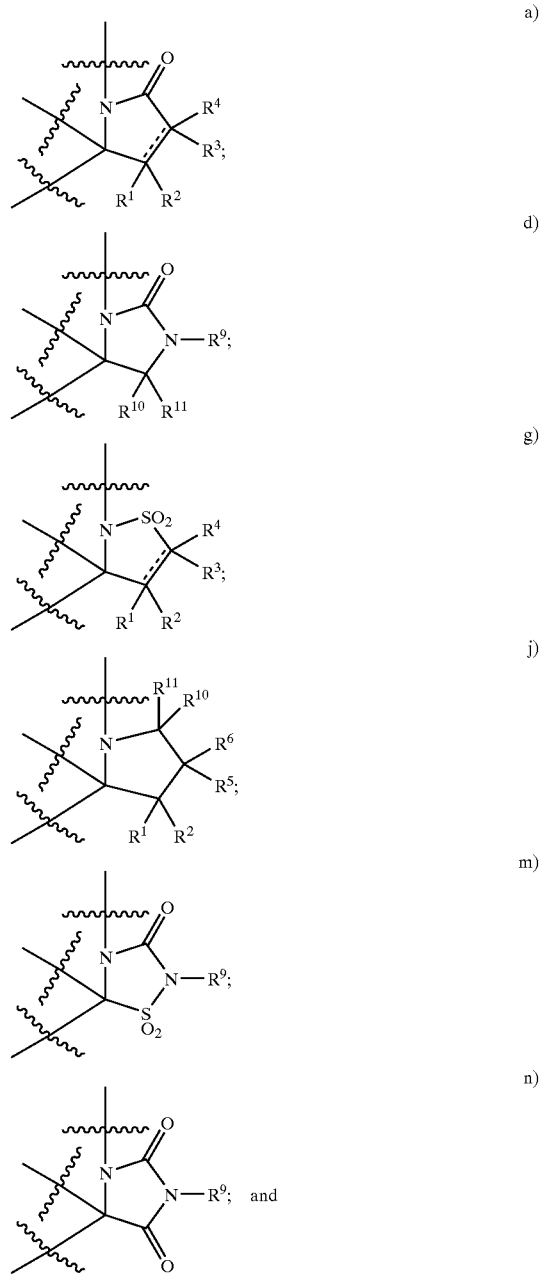

o)

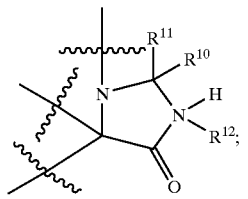

wherein each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_3-C_8)$cycloalkyl and $(C_1-C_{10})$heterocyclyl; wherein each of said $(C_1-C_4)$alkyl, $(C_6-C_{10})$aryl, $(C_3-C_8)$cycloalkyl and $(C_1-C_{10})$heterocyclyl may be optionally substituted on any of the ring carbon atoms capable of forming an additional bond with 1–3 substituents per ring independently selected from halo, $(C_1-C_4)$alkyl, $(C_1-C_4)$alkoxy, —CN, —OH and —NH$_2$; X is $(C_6-C_{10})$aryl or $(C_1-C_{10})$heteroaryl; Y is selected from the group consisting of a bond, oxygen, sulfur, >C=O, >SO$_2$, >S=O, —CH$_2$—, —CH$_2$O—, —O(CH$_2$)$_n$—, —CH$_2$S—, —S(CH$_2$)$_n$—, —CH$_2$SO—, —CH$_2$SO$_2$—, —SO(CH$_2$)$_n$—, —SO$_2$(CH$_2$)$_n$—, —NR$^{14}$—, —NR$^{14}$(CH$_2$)$_n$—, —CH$_2$[N(R$^{14}$)]—, —CH$_2$(CH$_2$)$_n$—, —CH=CH—, —C≡C—, —[N(R$^{14}$)]—SO$_2$— and —SO$_2$[N(R$^{14}$)]—; n is an integer from one to four; $R^{14}$ is hydrogen or $(C_1-C_4)$alkyl; Z is selected from the group consisting of $(C_6-C_{10})$aryl, $(C_3-C_8)$cycloalkyl, and $(C_1-C_{10})$heterocyclyl; wherein one or two carbon-carbon single bonds of said $(C_3-C_8)$cycloalkyl or $(C_1-C_{10})$heterocyclyl may optionally be replaced by carbon-carbon double bonds; wherein each of said X or Z may be independently optionally substituted on any of the ring carbon atoms capable of forming an additional bond by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy; G is $R^{15}$—(CR$^{16}$R$^{17}$)$_p$—; wherein G is a substituent on any ring carbon atom of Z capable of forming an additional bond and is oriented at a position other than alpha to the point of attachment of the Z ring to Y; p is an integer from 0 to 4; $R^{15}$ is independently selected from the group consisting of, halo, —CN, —NO$_2$, OH, $(C_1-C_4)$alkenyl, $(C_1-C_4)$alkynyl, $(C_1-C_4)$perfluoroalkyl, perfluoro$(C_1-C_4)$alkoxy, $R^{18}$—O—, $R^{18}$—$(C_1-C_4)$alkyl-O—, $R^{18}$—(C=O)—, $R^{18}$—(C=O)—O—, $R^{18}$—O—(C=O)—$R^{18}$—S—, $R^{22}$—(S=O)—, $R^{18}$—(SO$_2$)—, $R^{22}$—(SO$_2$)—(NR$^{21}$)—, $R^{19}$—(C=O)—(NR$^{21}$)—, $R^{22}$—O—(C=O)—(NR$^{21}$)—, (R$^{19}$R$^{20}$)N—, (R$^{19}$R$^{20}$)N—(SO$_2$)—, (R$^{19}$R$^{20}$)N—(C=O)—; (R$^{19}$R$^{20}$)N—(C=O)—(NR$^{21}$)— and (R$^{19}$R$^{20}$)N—(C=O)—O—; each of $R^{16}$ and $R^{17}$ are independently selected from hydrogen and $(C_1-C_4)$alkyl; or $R^{16}$ and $R^{17}$ may optionally be taken together with the carbon to which they are attached to form a 5 to 10-membered carbocyclic ring; $R^{18}$, $R^{19}$, $R^{20}$ and $R^{21}$ are independently selected from the group consisting of hydrogen, $(C_1-C_4)$alkyl, $(C_6-C_{10})$aryl, $(C_3-C_8)$cycloalkyl, and $(C_1-C_{10})$heterocyclyl; wherein said $(C_6-C_{10})$aryl, $(C_3-C_8)$cycloalkyl, and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, [$(C_1-C_4)$alkyl]$_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—; or $R^{19}$ and $R^{20}$ may optionally be taken together with the nitrogen to which they are attached to form a 3 to 8-membered heterocyclic ring; or $R^{19}$ and $R^{21}$ may optionally be taken together with the nitrogen, the carbon or the oxygen to which they are attached to form a 3 to 8-membered heterocyclic ring; $R^{22}$ is selected from the group consisting of $(C_1-C_4)$alkyl, $(C_6-C_{10})$aryl, $(C_3-C_8)$cycloalkyl, and $(C_1-C_{10})$heterocyclyl; wherein said $(C_6-C_{10})$aryl, $(C_3-C_8)$cycloalkyl, and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, [$(C_1-C_4)$alkyl]$_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—; or $R^{21}$ and $R^{22}$ may optionally be taken together with the nitrogen, the oxygen or the sulfur to which they are attached to form a 3 to 8-membered heterocyclic ring; or a pharmaceutically acceptable salt thereof.

2. The compound according to claim 1 wherein said "A" is a)

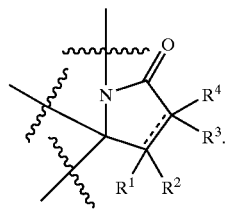

3. The compound according to claim 1 wherein said "A" is d)

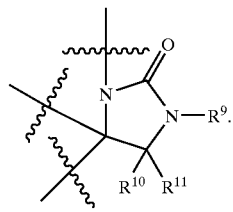

4. The compound according to claim 1 wherein said "A" is g)
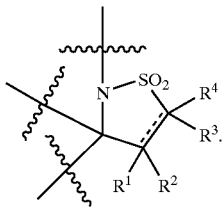

5. The compound according to claim 1 wherein said "A" is j)
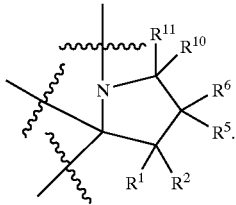

6. The compound according to claim 1 wherein said "A" is m)
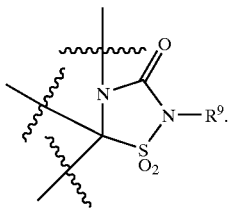

7. The compound according to claim 1 wherein said "A" is n)
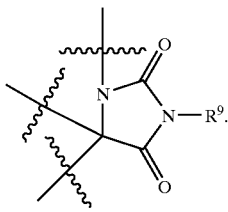

8. The compound according to claim 1 wherein said "A" is o)
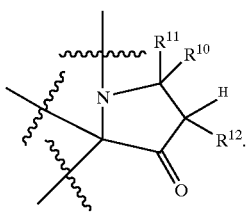

9. The compound according to claim 1 wherein said X is $(C_6-C_{10})$aryl.

10. The compound according to claim 1 wherein said X is phenyl.

11. The compound according to claim 1 wherein said X is $(C_1-C_{10})$heteroaryl.

12. The compound according to claim 11 wherein said $(C_1-C_{10})$heteroaryl is selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atoms capable of forming an additional bond by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy.

13. The compound according to claim 11 wherein said $(C_1-C_{10})$heteroaryl is selected from the group consisting of imidazolyl, isothiazolyl, isoxazolyl, oxadiazolyl, oxazolyl, pyrazinyl, pyridazinyl, pyridinyl, pyrimidinyl and pyrazolyl.

14. The compound according to claim 11 wherein said $(C_1-C_{10})$heteroaryl is selected from the group consisting of pyrazinyl, pyridazinyl, pyridyl and pyrimidinyl.

15. The compound according to claim 1 wherein said Y is selected from the group consisting of a bond, oxygen, $>C=O$, $-CH_2-$, $-CH_2O-$, $-O(CH_2)_n-$, $-CH_2CH_2-$, $-CH=CH-$ and $-C\equiv C-$; wherein n is 1 or 2.

16. The compound according to claim 15 wherein said Y is oxygen.

17. The compound according to claim 1 wherein said Y is selected from the group consisting of sulfur, $>SO_2$, $>S=O$, $-CH_2S-$, $-S(CH_2)_n-$, $-CH_2SO-$, $-CH_2SO_2-$, $-SOCH_2-$ and $-SO_2(CH_2)_n-$; wherein n is 1 or 2.

18. The compound according to claim 1 wherein said Y is selected from the group consisting of $-CH_2[N(R^{14})]-$, $>NR^{14}$, $-NR^{14}(CH_2)_n-$, $-SO_2[N(R^{14})]-$ and $-[N(R^{14})]-SO_2-$.

19. The compound according to claim 1 wherein said Z is selected from the group consisting of $(C_6-C_{10})$aryl or $(C_1-C_{10})$heteroaryl; and wherein said Z may be optionally substituted on any of the ring carbon atoms capable of forming an additional bond by one or two substituents per ring independently selected from the group consisting or F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy.

20. The compound according to claim 1 wherein said Z is $(C_6-C_{10})$aryl; wherein said Z is substituted on any of the ring carbon atoms capable of forming an additional bond by one or two substituents per ring independently selected from the group consisting of from F, Cl, CN, $(C_1-C_4)$alkyl, $(C_1-C_4)$perfluoroalkyl and $(C_1-C_4)$alkoxy.

21. The compound according to claim 1 wherein said G is $R^{15}-(CR^{16}R^{17})_p-$; wherein p is 0.

22. The compound according to claim 21 wherein said $R^{15}$ is selected from the group consisting of halo, $-CH$ and $R^{18}$; wherein $R^{18}$ is selected from the group consisting of hydrogen, $(C_1-C_4)$alkyl, $(C_6-C_{10})$aryl, $(C_3-C_8)$cycloalkyl, and $(C_1-C_{10})$heterocyclyl; wherein said $(C_6-C_{10})$aryl, $(C_3-C_8)$cycloalkyl, and $(C_1-C_4)$heterocyclyl moieties may be optionally substituted on any of the ring carbon atoms capable of forming an additional bond by one to three substituents per ring independently selected from the group consisting of from F, Cl, Br, CN, OH, ($C_1$–$C_4$)alkyl, ($C_1$–$C_4$)perfluoroalkyl, ($C_1$–$C_4$)perfluoroalkoxy, ($C_1$–$C_4$)alkoxy, amino, ($C_1$–$C_4$)alkyl-NH—, [($C_1$–$C_4$)alkyl]$_2$-N— and ($C_3$–$C_8$)cycloalkyloxy; wherein said ($C_3$–$C_8$)cycloalkyl and ($C_1$–$C_{10}$)heterocyclyl moieties may also optionally be substituted by oxo; wherein said ($C_1$–$C_{10}$)heteroaryl moiety may optionally be substituted on any ring nitrogen atom able to support an additional substituent by one to two substituents per ring independently selected from the group consisting of ($C_1$–$C_4$)alkyl and ($C_1$–$C_4$)alkyl-(C=O)—.

23. The compound according to claim 21, wherein said $R^{15}$ is selected from the group consisting of hydrogen, —CH, halo and oxadiazolyl.

24. The compound according to claim 21, wherein said G is oriented at a position meta to the point of attachment of the Z ring to Y.

25. The compound according to claim 21, wherein said G is oriented at a position para to the point of attachment of the Z ring to Y.

26. The compound according to claim 1 wherein said G is $R^{15}$—(CR$^{16}$R$^{17}$) and wherein p is an integer from 1 to 4.

27. The compound according to claim 26, wherein $R^{15}$ is selected from the group consisting of ($C_1$–$C_{10}$)heteroaryl; $R^{19}$—(C=O)—(NR$^{21}$)—, $R^{19}R^{20}$)N—, (R$^{19}$R$^{20}$)N—(C=O)—(NR$^{21}$)— and $R^{22}$—O—(C=O)—(NR$^{21}$); each $R^{16}$ and $R^{17}$ are independently hydrogen or ($C_1$–$C_4$)alkyl; $R^{19}$ is ($C_1$–$C_4$)alkyl or ($C_3$–$C_8$)cycloalkyl; $R^{20}$ is hydrogen or ($C_1$–$C_{10}$)heteroaryl selected from the group consisting of 2-oxazolyl, 2-pyrazolyl and 3-pyrazolyl; $R^{21}$ is hydrogen or ($C_1$–$C_4$)alkyl; and $R^{22}$ is ($C_1$–$C_4$)alkyl or ($C_3$–$C_8$)cycloalkyl.

28. The compound according to claim 26, wherein $R^{15}$ is 2-pyrazolyl; and each of $R^{16}$ and $R^{17}$ are independently hydrogen.

29. The compound according to claim 26, wherein $R^{15}$ has the formula $R^{19}$—(C=O)—(NR$^{21}$)—; each of $R^{16}$ and $R^{17}$ are independently hydrogen or ($C_1$–$C_4$)alkyl; $R^{19}$ is selected from the group consisting of methyl, ethyl, propyl, butyl and cyclobutyl; and $R^{21}$ is hydrogen.

30. The compound according to claim 26, wherein $R^{15}$ is selected from the group consisting of (R$^{19}$R$^{20}$)N—, (R$^{19}$R$^{20}$)N—(SO$_2$)—, (R$^{19}$R$^{20}$)N—(C=O)—; (R$^{19}$R$^{20}$)N—(C=O)—(NR$^{21}$)— and (R$^{19}$R$^{20}$)N—(C=O)—O—; wherein $R^{19}$ and $R^{20}$ are taken together with the nitrogen to which they are attached to form a 3 to 8-membered heterocyclic ring.

31. The compound according to claim 26, wherein $R^{15}$ is selected from the group consisting of $R^{19}$—(C=O)—NR$^{21}$—; $R^{22}$—(SO$_2$)—NR$^{21}$—; $R^{22}$—O—(C=O)=(NR$^{21}$)— and (R$^{19}$R$^{20}$)N—(C=O)—NR$^{21}$—; each of $R^{16}$ and $R^{17}$ are independently hydrogen or ($C_1$–$C_4$)alkyl; $R^{19}$ and $R^{21}$ are taken together with the nitrogen, the carbon or the oxygen to which they are attached to form a 3–8 membered heterocyclic ring; and $R^{21}$ and $R^{22}$ are taken together with the nitrogen, the carbon or the oxygen to which they are attached to form a 3–8 membered heterocyclic ring.

32. The compound according to claim 26, wherein G is oriented at a position meta to the point of attachment of the Z ring to Y.

33. The compound according to claim 26, wherein G is oriented at a position para to the point of attachment of the Z ring to Y.

34. The compound according to claim 1, wherein said compound is selected from the group consisting of:

1-[6-(4-Fluoro-phenoxy)-pyridin-3-yl]-1,7,9-triaza-spiro[4.5]decane-2,6,8,10-tetraone; 1-[6-(4-Fluoro-phenoxy)-pyridin-3-yl]-1,8,10-triaza-spiro[5.5]undecane-2,7,9,11-tetraone; 4-[5-(2,6,8,10-Tetraoxo-1,7,9-triaza-spiro[4.5]dec-1-yl)-pyridin-2-yloxy]-benzonitrile; 1-[6-(4-[1,3,4]oxadiazol-2-yl-phenoxy)-pyridin-3-yl]-1,7,9-triaza-spiro[4.5]decane-2,6,8,10-tetraone; 1-[6-(4-Ethyl-phenoxy)-pyridin-3-yl]-1,7,9-triaza-spiro[4.5]decane-2,6,8,10-tetraone; N-{4-[5-(2,6,8,10-Tetraoxo-1,7,9-triaza-spiro[4.5]dec-1-yl)-pyridin-2-yloxy]-benzyl}-acetamide; N-{4-[5-(2,6,8,10-Tetraoxo-1,7,9-triaza-spiro[4.5]dec-1-yl)-pyridin-2-yloxy]-benzyl}-propionamide; N-{4-[5-(2,6,8,10-Tetraoxo-1,7,9-triaza-spiro[4.5]dec-1-yl)-pyridin-2-yloxy]-benzyl}-butyramide; Pentanoic acid 4-[5-(2,6,8,10-tetraoxo-1,7,9-triaza-spiro[4.5]dec-1-yl)-pyridin-2-yloxy]-benzylamide; Cyclobutanecarboxylic acid 4-[5-(2,6,8,10-tetraoxo-1,7,9-triaza-spiro[4.5]dec-1-yl)-pyridin-2-yloxy]-benzylamide; 1-[6-(4-Bromo-phenoxy)-pyridin-3-yl]-1,7,9-triaza-spiro[4.5]decane-2,6,8,10-tetraone; 1-[6-(4-pyrazol-1-ylmethyl-phenoxy)-pyridin-3-yl]-1,7,9-triaza-spiro[4.5]decane-2,6,8,10-tetraone; and a pharmaceutically acceptable salt thereof.

* * * * *